(12) United States Patent
Gregory et al.

(10) Patent No.: US 11,236,175 B2
(45) Date of Patent: *Feb. 1, 2022

(54) T CELL MODIFYING COMPOUNDS AND USES THEREOF

(71) Applicant: Sangamo Therapeutics, Inc., Richmond, CA (US)

(72) Inventors: Philip D. Gregory, Richmond, CA (US); Michael C. Holmes, Richmond, CA (US)

(73) Assignee: Sangamo Therapeutics, Inc., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/453,603

(22) Filed: Mar. 8, 2017

(65) Prior Publication Data

US 2017/0183420 A1    Jun. 29, 2017

Related U.S. Application Data

(63) Continuation of application No. 14/051,244, filed on Oct. 10, 2013, now Pat. No. 9,597,357.

(60) Provisional application No. 61/712,028, filed on Oct. 10, 2012.

(51) Int. Cl.
| | |
|---|---|
| *C12N 5/00* | (2006.01) |
| *C07K 16/32* | (2006.01) |
| *C07K 16/28* | (2006.01) |
| *A61K 35/17* | (2015.01) |
| *C12N 5/0783* | (2010.01) |
| *A61K 48/00* | (2006.01) |
| *C12N 5/10* | (2006.01) |
| *A61K 35/26* | (2015.01) |

(52) U.S. Cl.
CPC ............. *C07K 16/32* (2013.01); *A61K 35/17* (2013.01); *A61K 35/26* (2013.01); *A61K 48/005* (2013.01); *C07K 16/2863* (2013.01); *C12N 5/0636* (2013.01); *C12N 5/10* (2013.01); *C07K 2317/622* (2013.01); *C07K 2317/64* (2013.01); *Y02A 50/30* (2018.01)

(58) Field of Classification Search
USPC .................................................... 424/93.21
See application file for complete search history.

(56) References Cited

U.S. PATENT DOCUMENTS

| | | |
|---|---|---|
| 5,356,802 A | 10/1994 | Chandrasegaran |
| 5,420,032 A | 5/1995 | Marshall et al. |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas et al. |
| 6,200,759 B1 | 3/2001 | Dove |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,794,136 B1 | 9/2004 | Eisenberg et al. |
| 6,824,978 B1 | 11/2004 | Cox, III et al. |
| 6,833,252 B1 | 12/2004 | Dujon et al. |
| 6,903,185 B2 | 6/2005 | Kim et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,153,949 B2 | 12/2006 | Kim et al. |
| 7,163,824 B2 | 1/2007 | Cox, III et al. |
| 7,253,273 B2 | 8/2007 | Collingwood |
| 7,262,054 B2 | 8/2007 | Jamieson et al. |
| 7,361,635 B2 | 4/2008 | Miller et al. |
| 7,514,537 B2 | 4/2009 | Jensen |
| 7,914,796 B2 | 3/2011 | Miller et al. |
| 7,951,925 B2 | 5/2011 | Ando et al. |
| 8,110,379 B2 | 2/2012 | DeKelver et al. |
| 2003/0068675 A1 | 4/2003 | Liu |
| 2003/0232410 A1 | 12/2003 | Aspland et al. |
| 2004/0002092 A1 | 1/2004 | Arnould et al. |
| 2005/0026157 A1 | 2/2005 | Baltimore et al. |
| 2005/0064474 A1 | 3/2005 | Urnov et al. |

(Continued)

FOREIGN PATENT DOCUMENTS

| | | |
|---|---|---|
| EP | 2 352 369 A1 | 8/2011 |
| EP | 2 419 511 A1 | 2/2012 |

(Continued)

OTHER PUBLICATIONS

Porteus (Nature Biotech., 2005, vol. 23, No. 8, p. 967-973.*
Ramirez (Unexpected failure rates for modular assembly of engineered zinc fingers. Nature Methods, 2008, 5(5): 374-375).*
Geurts (Science, Jul. 24, 2009, vol. 325, p. 433).*
Christian (Genetics, available online Jul. 26, 2008, vol. 186, p. 757-761).*
Weber (Seminars in Oncology, Oct. 2010, vol. 37, No. 5, p. 430-439).*
Turtle (Curr. Opin. Immunol., 2012, Available online Jul. 18, 2012, vol. 24, p. 633-639).*

(Continued)

*Primary Examiner* — Michael C Wilson
(74) *Attorney, Agent, or Firm* — Foley & Lardner LLP

(57) ABSTRACT

Methods and compositions for modifying T-cells in which PD1 and/or CTLA-4 is repressed and/or inactivated using fusion proteins such as artificial transcription factors and nucleases.

12 Claims, 2 Drawing Sheets

Specification includes a Sequence Listing.

(56) References Cited

U.S. PATENT DOCUMENTS

| | | |
|---|---|---|
| 2005/0208489 A1 | 9/2005 | Carroll et al. |
| 2006/0063231 A1 | 3/2006 | Li et al. |
| 2006/0078558 A1 | 4/2006 | Arnould et al. |
| 2006/0153826 A1 | 7/2006 | Arnould et al. |
| 2006/0188987 A1 | 8/2006 | Guschin et al. |
| 2006/0206949 A1 | 9/2006 | Arnould et al. |
| 2007/0116690 A1* | 5/2007 | Yang .................. A01K 67/0271 424/93.21 |
| 2007/0117128 A1 | 5/2007 | Smith et al. |
| 2007/0218528 A1 | 9/2007 | Miller |
| 2008/0131962 A1 | 6/2008 | Miller |
| 2008/0159996 A1 | 7/2008 | Ando et al. |
| 2008/0188000 A1* | 8/2008 | Reik .................... C07K 14/721 435/463 |
| 2008/0299580 A1 | 12/2008 | DeKelver et al. |
| 2008/0311095 A1 | 12/2008 | Holmes et al. |
| 2009/0068164 A1 | 3/2009 | Segal et al. |
| 2009/0305346 A1 | 12/2009 | Miller |
| 2010/0047805 A1 | 2/2010 | Wang |
| 2010/0218264 A1 | 8/2010 | Cui et al. |
| 2010/0260731 A1 | 10/2010 | Braspenning et al. |
| 2011/0033884 A1* | 2/2011 | Wood .................. G01N 33/505 435/29 |
| 2011/0136895 A1 | 6/2011 | Gregory et al. |
| 2011/0158957 A1 | 6/2011 | Bonini et al. |
| 2011/0201055 A1 | 8/2011 | Doyon et al. |
| 2011/0207221 A1 | 8/2011 | Cost et al. |
| 2011/0281361 A1 | 11/2011 | DeKelver et al. |
| 2011/0301073 A1 | 12/2011 | Gregory et al. |
| 2011/0301703 A1 | 12/2011 | Glazier |
| 2012/0213783 A1 | 8/2012 | Rosenberg et al. |
| 2013/0122591 A1* | 5/2013 | Cost ......................... C12N 9/96 435/456 |
| 2013/0137104 A1 | 5/2013 | Cost et al. |
| 2013/0177960 A1 | 7/2013 | Rebar |
| 2013/0177983 A1 | 7/2013 | Rebar |
| 2013/0280220 A1 | 10/2013 | Ahmed et al. |
| 2013/0315884 A1* | 11/2013 | Galetto ................ C12N 5/0636 424/93.71 |
| 2015/0071889 A1* | 3/2015 | Musunuru ............ C12N 15/907 424/93.7 |

FOREIGN PATENT DOCUMENTS

| | | |
|---|---|---|
| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A | 8/2001 |
| WO | WO 88197 A2 | 11/2001 |
| WO | WO 02/016536 A1 | 2/2002 |
| WO | WO-02/42459 A2 | 5/2002 |
| WO | WO 02/077227 A2 | 10/2002 |
| WO | WO 02/099084 A2 | 12/2002 |
| WO | WO 03/016496 A2 | 2/2003 |
| WO | WO-03/022875 A2 | 3/2003 |
| WO | WO 05/017791 A2 | 2/2005 |
| WO | WO 07/014275 A2 | 2/2007 |
| WO | WO 08/153742 A2 | 12/2008 |
| WO | 2010027423 A2 | 3/2010 |
| WO | 2011045704 A1 | 4/2011 |
| WO | 2012012667 A2 | 1/2012 |
| WO | WO 12/099973 A2 | 7/2012 |

OTHER PUBLICATIONS

Brandl (FEBS Open Bio., 2015, vol. 5, p. 26-35).*
Chiang (Scientific Reports, Feb. 29, 2016, p. 1-12).*
Goh ("CRISPR—What can go wrong and how to deal with it", Apr. 11, 2017, p. 1-7).*
Turtle, et al., "Engineered T Cells for Anti-Cancer Therapy," Curr. Opin. Immunol., 24(5):633-639 (2012).
ArAST et al., "1-PPOL and 1-CREL Homing Site Sequence Degeneracy Determined by Random Mutagensis and Sequential In Vitro Enrichment," J. Mol. Biol. 280:345-353 (1998).
Ashworth et al., "Computational Redesign of Endonuclease DNA Binding Cleavage Specificity," Nature 441:656-659 (2006).
Attia et al., "Autoimmunity Correlates With Tumor Regression in Patients With Metastatic Melanoma Treated With Anti-Cytotoxic T-Lymphocyte Antigen-4," J. Clin. Oncol. 23(25):6403-6053 (2005).
Barber et al., "Restoring Function in Exhausted CD8 T Cells During Chronic Viral Infection," Nature 439(9):682-687 (2006).
Beerli et al., "Engineering Polydactyl Zinc-Finger Transcription Factors," Nature Biotechnol. 20:135-141(2002).
Belfort et al., "Homing Endonucleases: Keeping the House in Order," Nucleic Acids Research 25:3379-3388 (1997).
Berger et al., "Adoptive Transfer of Virus-Specific and Tumor-Specific T Cell Immunity," Curr. Opin. Immunol. 21(2):224-232 (2009); doi: 10.1016/j.coi.2009.02.10.
Bhattacharyya et al., "T-Cell Immunotherapy With a Chimeric Receptor Against CD38 Is Effective in Eradicating Chemotherapy-Resistant B-Cell Lymphoma Cells Overexpressing Survivin Induced By BMI-1," Blood Cancer Journal 2(6):e75 (2012).
Bitinaite et al., "Poki Dimerization Is Required for DNA Cleavage," PNAS USA 95:10570-10575 (1998).
Bonas et al., "Genetic and Structural Characterization of the Avirulence Gene AVRBS3 From Xanthomonas campestris Pv. Vesicatoria" Mol. Gen. Genet. 218:127-136 (1989).
Brouns et al., "Small CRISPR RNAS Guide Antiviral Defense in Prokaryotes," Science 321:960-964 (2008).
Chang et al., "Modicication of DNA Ends Can Decrease End Joining Relative to Homologous Recombination in Mammalian Cells," PNAS USA 84:4959-4963 (1987).
Chevalier et al., "Design, Activity, and Structure of a Highly Specific Artificial Endonuclease," Molecular Cell 10:895-905 (2002).
Chicaybam et al., "Chimeric Antigen Receptors in Cancer Immuno-Gene Therapy: Current Status and Future Directions," Int. Rev. Immunol. 30:294-311 (2011).
Choo et al., Advances in Zinc Finger Engineering, Curr. Opin. Struct. Biol. 10:411-416 (2000).
Cong et al., "Multiplex Genome Engineering Using CRISPR/CAS Systems," Sciencexpress/10.1126/science.1231143 (2013).
Dotti, "Blocking PD-1 in Cancer Immunotherapy," Blood 114(8):1457-58 (2009).
Dujon et al., "Mobile Introns: Definition of Terms and Recommended Nomenclature," Gene 82:115-118 (1989).
Dutour et al., "In Vitro and In Vivo Antitumor Effect of Anti-CD33 Chimericreceptor-Expressing EBV-CTL Against CD33+ Acutemyeloid Leukemia," Adv. Hematol. 2012:683065 (2012).
Epinant et al., "A Novel Engineered Meganuclease Induces Homologous Recombination in Yeast and Mammalian Cells," Nucleic Acids Research 31:2952-2962 (2003).
Freeman et al., "Reinvigorating Exhausted HIV-Specific T Cells Via PD-1-PD-1 Ligand Blockade," J. Exp. Med. 203(10):2223-2227 (2006).
Gimble et al., "Substrate Recognition and Induced DNA Distortion By Pi-Scel Endonuclease, An Enzyme Generated by Protein Splicing," J. Mol. Biol. 263:163-180 (1996).
Godde and Bickerton, "The Repetitive DNA Elements Called CRISPRS and Their Associated Genes: Evidence of Horizontal Transfer Among Prokaryotes," J. Mol. Evol. 62:718-729 (2006).
Haft et al., "A Guild of 45 CRISPR-Associated (CAS) Protein Families and Multiple CRISPR/CAS Subtypes Exist in Prokaryotic Genomes," PLoS Comput. Biol. 1:e60 (2005) <http://www.jevi.org/ems/nc/publications/listing/browse/3/article/Haft/#sthash.b.XXP6pOi.dpuf>.
Hale et al., "Prokaryotic Silencing (PSI)RNAS in Pyrococcus Furiosus", RNA 14:2572-2579 (2008).
Haso et al., "Generation and Optimization of a Chimeric Antigen Receptor Against Human CD22: A New Immunotherapeutic Agent

(56) References Cited

OTHER PUBLICATIONS for Adoptive Immunotherapy," *Canc. Res.* 72(8):Supplement 1 (2012) doi: 1158/1158-7445 AM 2012-3504.
Heuer et al., "Repeat Domain Diversity of AVRBS3-Like Genes in Ralstonia Solanacearum Strains and Association With Host Preferences in the Field," *Appl. and Envir. Micro.* 73(13):4379-4384 (2007).
Huang et al., "Genetically Modified T Cells Targeting Interleukin-11 Receptor A-Chain Kill Human Osteosarcoma Cells and Induce the Regression of Established Osteosarcoma Lung Metastases," *Cancer Res.* 72(1):271-281 (2012).
Isalan et al., "A Rapid, Generally Applicable Method to Engineer Zinc Fingers Illustrated by Targeting The HIV-1 Promoter," *Nature Biotechnol.* 19:656-660 (2001).
Jansen et al., "Identification of Genes That Are Associated With DNA Repeats in Prokaryotes," *Mol. Microbiol.* 43:1565-1575 (2002).
Jasin, "Genetic Manipulation of Genomes With Rare-Cutting Endonucleases," *Trends Genet.* 12:224-228 (1996).
Jinek et al., "A Programmable Dual-RNA-Guided DNA Endonuclease in Adaptive Bacterial Immunity," *Science* 37:816 (2012).
June, "Adoptive T Cell Therapy for Cancer in the Clinic," *The Journal of Clinic Investigation* 117:1466-1476 (2007), doi: 10.1172/JCI32446.
Kalos, et al., "T Cells With Chimeric Antigen Receptors Have Potent Antitumor Effects and Can Establish Memory in Patients With Advanced Leukemia," *Science Translational Medicine* 3(95):95ra72 (2011).
Kay et al., "A Bacterial Effector Acts As a Plant Transcription Factor and Induces a Cell Size Regulator," *Science* 318:648-651 (2007).
Kiessling et al., "Tumor-Associated Antigens for Specific Immunotherapy of Prostate Cancer," *Cancers* 4:193-217 (2012).
Kim et al., "Insertion and Deletion Mutants of Foki Restriction Endonuclease," *J. Biol. Chem.* 269:31978-31982 (1994).
Kim, "Chimeric Restriction Endonuclease," *PNAS* 91:883-887 (1994).
Lamers et al., "Immune Responses to Transgene and Retroviral Vector In Patients Treated With XVIVO-Engineered T Cells," *Blood* 117(1):72-82 (2011).
Lei et al., "Repurposing CRISPR As An RNA-Guided Platform for Sequence-Specific Control of Gene Expression," *Cel* 152(5):1173-1183 (2013).
Li et al., "Functional Domains in FOK I Restriction Endonuclease," *PNAS USA* 89:4275-4279 (1992).
Li et al., "Alteration of the Cleavage Distance of FOK I Restriction Endonuclease by Insertion Mutagenesis," *PNAS USA* 90:2764-2768 (1993).
Lillestol et al., "A Putative Viral Defence Mechanism in Archaeal Cells," *Archaea* 2:59-72 (2006).
Louis et al., "Antitumor Activity and Long-Term Fate of Chimeric Antigen Receptor-Positive T Cells in Patients With Neuroblastoma," *Blood* 118(23):650-656 (2011).
Makarova et al., "A DNA Repair System Specific for the Thermophilic Archaea and Bacteria Predicted By Genomic Context Analysis," *Nucleic Acids Res.* 30:482-496 (2002).
Makarova et al., "A Putative RNA-Interference-Based Immune System Inprokaryotes: Computational Analysis of the Predicted Enzymatic Machinery, Functional Analogies With Eukaryotic RNAI, and Hypothetical Mechanisms of Action," *Biol. Direct.* 1:7 (2006).
Miller et al., "An Improved Zinc-Finger Nuclease Architecture For Highly Specific Genome Editing," *Nat. Biotechnol.* 25:778-785 (2007).
Nehis et al., "Two Genetically Separable Steps in the Differentiation of Thymic Epithelium," *Science* 272:886-889 (1996).
Okazaki et al., "PD-1 and PD-1 Ligands: From Discovery to Clinical Application," *International Immunology* 19(7):813-824 (2007).
Oleykowski et al., "Mutation Detection Using a Novel Plant Endonuclease," *Nucleic Acids Res.* 26(20):4597-4602 (1998).
Orentas et al., "Immunotherapy Targets in Pediatric Cancer," *Front in Oncol.* 2:1 (2012) doi: 10.3389/fone.2012.00003.
Pabo et al., "Design and Selection of Novel CYS2HIS2 Zincfinger Proteins," *Ann. Rev. Biochem.* 70:313-340(2001).
Paques et al., "Meganucleases and DNA Double-Strand Break-Induced Recombination: Perspectives for Gene Therapy," *Current Gene Therapy* 7:49-66 (2007).
Pardoll, "The Blockade of Immune Checkpoints in Cancer Immunotherapy," *Nat. Rev. Cancer* 12(4):252-264 (2012).
Perler et al., "Protein Splicing Elements: Inteins and Exteins—A Definition of Terms and Recommended Nomenclature," *Nucleic Acids Research* 22:1125-1127 (1994).
Petrovas et al., "Differential Association of Programmed Death-1 And CD57 With Ex Vivo Survival of $CD8^+$ T Cells In HIV Infection" *J. Immunol.* 183(2):1120-32 (2009).
Porteus et al., "Gene Targeting Using Zinc Finger Nucleases," *Nat. Biotechnol.* 23:967-973 (2005).
Qi et al., "Repurposing CRISPR As An RNA-Guided Platform for Sequence-Specific Control of Gene Expression," *Cell* 152:1173-1183 (2013).
Qui et al., "Mutation Detection Using Surveyor Nuclease," *Biotechniques* 36(4):702-707 (2004).
Ramos and Dotti, "Chimeric Antigen Receptor (CAR)-Engineered Lymphocytes for Cancer Therapy," *Expert Opin. Bio. Ther.* 11(7):855 (2011).
Rhodes et al., "Regulation of Immunity by Butyrophilins," *Annual Review of Immunology* 34:6.1-6.22 (2016).
Rosenberg et al., "Durable Complete Responses in Heavily Pretreated Patients With Metastatic Melanoma Using T Cell Transfer Immunotherapy," *Clin. Canc. Res.* 17(13):4550-4557 (2011).
Salvoldo et al., "CD28 Costimulation Improves Expansion and Persistence of Chimeric Antigen Receptor-Modified T Cells In Lymphoma Patients," *J. Clin. Invest.* 121(5):1822-1826 (2011).
Schornack et al., "Gene-For-Gene-Mediated Recognition of Nuclear-Targeted AVRBS3-Like Bacterial Effector Proteins," *J. Plant Physiol.* 163(3):256-272 (2006).
Schuberth et al., "Effector Memory and Central Memory NY-ESO-1-Specific Re-Directed T Cells For Treatment Of Multiple Myeloma," *Gene Ther.* 20(4):386-395 (2013) doi: 10.1038/gt.2012.48.
Segal, "Custom DNA-Binding Proteins Come of Age: Polydactyl Zinc-Finger Proteins," *Curr. Opin. Biotechnol.* 12:632-637 (2001).
Shaffer et al., "T Cells Redirected Against CD70 For The Immunotherapy Of CD70-Positive Malignancies," *Blood* 116(16):4304-4314 (2011).
Sharma et al., "Novel Cancer Immunotherapy Agents With Survival Benefit: Recent Successes and Next Steps," *Nature Reviews Cancer* 11(11):805-812 (2011).
Sorek et al., "CRISPR—A Widespread System That Provides Acquired Resistance Against Phages in Bacteria and Archaea," *Nat. Rev. Microbiol.* 6:181-186 (2008).
Stein et al., "Antiproliferative Activity of a Humanized Anti-CD74 Monoclonal Antibody, HLL1, On B-Cell Malignancies," *Blood* 104:3705-3711 (2004).
Sussman et al., "Isolation and Characterization of New Homing Endonuclease Specificities At Individual Target Site Positions," *J. Mol. Biol.* 342:31-41 (2004).
Tang et al., "Identification of Novel Non-Coding RNAS As Potential Antisense Regulators In The Archaeon Sulfolobus Solfataricus," *Mol. Microbiol.* 55(2):469-481 (2002).
Tang et al., "Identification of 86 Candidates for Small Non-Messenger RNAS From The Archaeon Archaeoglobus Fulgidus," *PNAS USA* 99:7536-7541 (2002).
Till et al., "CD20-Specific Adoptive Immunotherapy for Lymphoma Using a Chimeric Antigen Receptor With Both CD28 AND4-IBB Domains: Pilot Clinical Trial Results," *Blood* 119(17):3940-3950 (2012).
Topolian et al., "Immune Checkpoint Blockade: A Common Denominator Approach to Cancer Therapy," *Cancer Cell* 27(4):450-461 (2015).
Torikai et al., "A Foundation For Universal T-Cell Based Immunotherapy: T Cells Engineered To Express A CD19-Specific Chimeric-AntigenReceptor And Eliminate Expression Of Endogenous TCR," *Blood* 119(24):5697-5705(2012).
Weber, "Immune Checkpoint Proteins: A New Therapeutic Paradigm for Cancer—Preclinical Background: CTLA-4 And PD-1 Blockade," *Seminars in Oncology* 37(5):430-439 (2010).

(56) References Cited

OTHER PUBLICATIONS

Weber, "Review: Anti-CTLA-4 Antibody Ipilimumab: Case Studies of Clinical Response and Immune-Related Adverse Events," *Oncologist* 12(7):864-872 (2007).

Wolfe, "PD-I Immunotherapy Makes a Splash At ASCO," *Oncology Business Review* 6(4) (Jul. 2012) <http://obroncology.com/obrgreen/article/PD-1-Immunotherapy-Makes-a-Splash-at-ASCO>.

Wu et al., "Adoptive T-Cell Therapy Using Autologous Tumor-Infiltrating Lymphocytes for Metastatic Melanoma: Current Status and Future Outlook," *Cancer J.* 18(2):160-175 (2012).

Yeung et al., "Enzymatic Mutation Detection Technologies," *Bio Techniques* 38(5):749-758 (2005).

Zhao et al., "A Herceptin-Based Chimeric Antigen Receptor With Modified Signaling Domains Leads To Enhanced Survival Of Transduced T Lymphocytes And Antitumor Activity," *J. Immunol.* 183(9):5563-5574 (2009).

Lloyd, et al., "Beyond the Antigen Receptor: Editing the Genome of T-Cells for Cancer Adoptive Cellular Therapies," *Frontiers in Immunology* (4):1-7 (2013).

Menger, et al., "Talen-Mediated Inactivation of PD-1 in Tumor-Reactive Lymphocytes Promotes Intratumoral T-Cell Persistence and Rejection of Established Tumors," *Cancer Research* 76(8):2087-2093 (2016).

\* cited by examiner

SEQUENCE LISTING

```
<160> NUMBER OF SEQ ID NOS: 123

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Ser Ser Asp Leu Ser Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ser Asp Asn Leu Arg Glu
1               5

<210> SEQ ID NO 3
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 3

Arg Ser Asp Asp Leu Ser Lys
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Ser Asp Leu Arg Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Lys Gln His Leu Asn Glu
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Arg Ser Ala Leu Ser Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ser Asp Ala Leu Ala Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Ser Gly Asp Arg Asn Lys
1               5
```

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Arg Ser Asn Leu Ser Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Asp Asp Arg Lys Thr
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Ser Gly Ser Leu Thr Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ser Asp Asn Leu Thr Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Asn Ala Thr Arg Ile Lys
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 14

Arg Ser Asp Val Leu Ser Ala
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Arg Ser Asn Arg Ile Lys
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ser Ala Asn Leu Ala Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Asn Gln Asn Arg Ile Thr
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Ser Gly His Leu Ser Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ser Asp Ser Leu Leu Arg
1               5

<210> SEQ ID NO 20
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Asn Asp Asp Arg Lys Lys
1               5

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
acagtgcttc ggcaggctga cagccagg                                      28

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
acccggacct cagtggcttt gcctggag                                      28

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
actacctggg cataggcaac ggaaccca                                      28

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tggcggtggg tacatgagct ccaccttg                                      28

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gtagcaccgc ccagacgact g                                             21

<210> SEQ ID NO 26
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gtgctccagg catgcagatc c                                              21

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
atgcagatcc cacaggcgc                                                 19

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gttgtagcac cgcccagacg a                                              21

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gttgtagcac cgcccagacg                                                20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cttctcccca gccctgctcg t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gtgaaggtgg cgttgtcccc t                                              21

<210> SEQ ID NO 32
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 32
ctacctctgt ggggccatct c                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ctctctttga tctgcgcctt g                                              21

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Ser Gly His Leu Ser Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Ser Asp Ser Leu Ser Val
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

His Asn Asp Ser Arg Lys Asn
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Ser Asp Asp Leu Thr Arg
1               5
```

```
<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ser Asp His Leu Thr Gln
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Ser Ala Ala Leu Ser Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Ser Asp His Leu Thr Thr
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Arg Ser Ala Leu Ala Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Ser Ala Ala Leu Ala Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43
```

```
Arg Asn Asp His Arg Lys Asn
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ser Asp His Leu Ser Glu
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Ser Ser Asp Arg Thr Lys
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ser Ala Ser Arg Lys Asn
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Ser Asp Val Leu Ser Glu
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Ser Ala Asn Leu Thr Arg
1               5

<210> SEQ ID NO 49
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 49

Arg Ser Asp His Leu Ser Gln
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Thr Ser Ser Asn Arg Lys Thr
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Asp Trp Asn Leu Ser Gln
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ser Ser Ala Leu Ser Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Pro Leu Ala Leu Lys His
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Thr Arg Pro Val Leu Lys Arg
1               5
```

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Ala Asn Ser Leu Leu Arg
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Pro Ser Thr Leu His Arg
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ser Asp Glu Leu Thr Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Asn Asn Asn Leu Arg Thr
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Asn Trp His Leu Arg Thr
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 60

Arg Thr Pro His Leu Thr Leu
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Ser Ala Gln Leu Ala Thr
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Cys Thr His Leu Tyr Leu
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Pro Thr Gln Arg Tyr Ser
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Ala Asn His Arg Glu Cys
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Lys Phe Ala Arg Pro Ser
1               5

<210> SEQ ID NO 66
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 66

Arg Asn Phe Ser Arg Ser Asp
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

His Pro His His Arg Met Cys
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Met Gly Arg Leu Ser Thr
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg His Ser Arg Leu Thr Thr
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Arg Pro Val Leu Met Arg
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Arg Ala Asn His Arg Val Cys
1               5
```

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Arg Ser Thr His Leu Leu Gly
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Asn Ala Ala Leu Thr Arg
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Ser Cys Gly Leu Trp Ser
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Cys Asn Ala Ala Leu Thr Arg
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Glu Glu His Arg Ala Thr
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 77

Arg His His His Leu Ala Ala
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Arg Pro Met His Leu Thr Asn
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Ser Pro His Leu Tyr His
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Arg Cys Glu Ala Leu His His
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Asp Arg Ser Ala Gln Ala Arg
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Leu Pro Ala Leu Leu Ser
1               5

<210> SEQ ID NO 83
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

His Asn Ala Ala Leu Thr Arg
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Thr Tyr Asn Arg Thr Gln
1               5

<210> SEQ ID NO 85
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ccagggcgcc tgtgggatct gcatgcct                                      28

<210> SEQ ID NO 86
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
cagtcgtctg ggcggtgcta caactggg                                      28

<210> SEQ ID NO 87
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gaacacaggc acggctgagg ggtcctcc                                      28

<210> SEQ ID NO 88
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ctgtggacta tggggagctg gatttcca                                      28

<210> SEQ ID NO 89
```

<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
cagtcgtctg ggcggtgct                                            19

<210> SEQ ID NO 90
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
arcaccrccc aracrac                                              17

<210> SEQ ID NO 91
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
rctccarrca trcarat                                              17

<210> SEQ ID NO 92
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
rcaratccca carrc                                                15

<210> SEQ ID NO 93
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
trtarcaccr cccarac                                              17

<210> SEQ ID NO 94
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
trtarcaccr cccara                                               16

<210> SEQ ID NO 95
<211> LENGTH: 17

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
tctccccarc cctrctc                                                  17

<210> SEQ ID NO 96
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
raarrtrrcr ttrtccc                                                  17

<210> SEQ ID NO 97
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
acctctrtrr rrccatc                                                  17

<210> SEQ ID NO 98
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ctctttratc trcrcct                                                  17

<210> SEQ ID NO 99
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
accrcatrar ccccarc                                                  17

<210> SEQ ID NO 100
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
crrrraarrc rrccarc                                                  17

<210> SEQ ID NO 101
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 101

Arg Ser Asp Thr Leu Ser Val
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Asp Asn Ser Thr Arg Ile Lys
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Ser Asp Val Arg Lys Asn
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Asp Arg Ser His Leu Thr Arg
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Arg Ser Asp His Leu Ser Arg
1               5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Arg Ser Asp Asn Leu Ala Arg
1               5
```

```
<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Ser Gly Asn Leu Ala Arg
1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gln Ser Gly Asp Leu Thr Arg
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Arg Ser Asp Asn Leu Ser Val
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Ser Asp Val Leu Ser Lys
1               5

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ala Arg Ser Thr Arg Thr Asn
1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 112

Asp Arg Ser His Leu Ala Arg
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Arg Ser Asp Asn Leu Ser Glu
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Ser Asp His Leu Ser Thr
1               5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Asp Arg Ser Asn Arg Lys Thr
1               5

<210> SEQ ID NO 116
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ggtagggcgt gggggccacg ggcccacc                                      28

<210> SEQ ID NO 117
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
atgtggagga agaggggggcg ggagcaag                                     28

<210> SEQ ID NO 118
<211> LENGTH: 28
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 118
gagcagtgga gaaggcggca ctctggtg                                            28

<210> SEQ ID NO 119
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gtggagaagg cggcactctg gtggggct                                            28

<210> SEQ ID NO 120
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
acaactgggc tggcggccag gatggttc                                            28

<210> SEQ ID NO 121
<211> LENGTH: 9
<212> TYPE: PRT
<213> ORGANISM: Unknown
<220> FEATURE:
<223> OTHER INFORMATION: Description of Unknown: 'LAGLIDADG'
      family motif peptide

<400> SEQUENCE: 121

Leu Ala Gly Leu Ile Asp Ala Asp Gly
1               5

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gtaccgcatg agccccagca a                                                   21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ctcggggaag gcggccagct t                                                   21
```

T CELL MODIFYING COMPOUNDS AND USES THEREOF

CROSS-REFERENCE TO RELATED APPLICATIONS

The present application is a continuation of U.S. patent application Ser. No. 14/051,244, filed Oct. 10, 2013, which claims the benefit of U.S. Provisional Application No. 61/712,028, filed Oct. 10, 2012, the disclosures of which are hereby incorporated by reference in their entireties.

TECHNICAL FIELD

The present disclosure is in the fields of genome editing and therapeutics.

BACKGROUND

Engineered nucleases, including zinc finger nucleases, TALENs and homing endonucleases designed to specifically bind to target DNA sites are useful in genome engineering. For example, zinc finger nucleases (ZFNs) are proteins comprising engineered site-specific zinc fingers fused to a nuclease domain. Such ZFNs and TALENs have been successfully used for genome modification in a variety of different species. See, for example, United States Patent Publications 20030232410; 20050208489; 20050026157; 20050064474; 20060188987; 20060063231; 20110301073; 20130177983; 20130177960; 20150056705 and International Publication WO 07/014275, the disclosures of which are incorporated by reference in their entireties for all purposes. These engineered nucleases can create a double-strand break (DSB) at a specified nucleotide sequence, which increases the frequency of homologous recombination at the targeted locus by more than 1000-fold. Thus, engineered nucleases can be used to exploit the homology-directed repair (HDR) system and facilitate targeted integration of transgenes into the genome of cells. In addition, the inaccurate repair of a site-specific DSB by non-homologous end joining (NHEJ) can also result in gene disruption.

The programmed death receptor (PD1 or PD-1, also known as PDCD1) has been shown to be involved in regulating the balance between T-cell activation and T-cell tolerance in response to chronic antigens, and is encoded by one of a group of genes known as immunological checkpoint genes. The proteins encoded by these genes are involved in regulating the amplitude of immune responses. Upon T-cell activation, PD1 expression is induced in T-cells. The ligands for the PD1 receptor are PD1 ligand (PDL1 also known as B7-H1 and CD272) and PDL2 (also known as B7-DC and CD273), and are normally expressed in antigen presenting cells. PD1-PDL (PD1 ligand) coupling causes deactivation of the T-cell and is involved in inducing T-cell tolerance (see, Pardoll (2012) Nat Rev 12:252). During HIV1 infection, expression of PD1 has been found to be increased in CD4+ T-cells, and PDL1 expression is increased in APCs, tipping the balance between T-cell inhibition and T-cell stimulation towards T-cell inhibition (see Freeman et al (2006) J Exp Med 203(10):2223-2227). It is thought that PD1 up-regulation is somehow tied to T-cell exhaustion (defined as a progressive loss of key effector functions) when T-cell dysfunction is observed in the presence of chronic antigen exposure as is the case in HIV infection. PD1 up-regulation may also be associated with increased apoptosis in these same sets of cells during chronic viral infection (see Petrovas et al, (2009) J Immunol. 183(2): 1120-32). PD1 may also play a role in tumor-specific escape from immune surveillance. It has been demonstrated that PD1 is highly expressed in tumor-specific cytotoxic T lymphocytes (CTLs) in both chronic myelogenous leukemia (CIVIL) and acute myelogenous leukemia (AML). PD1 is also up-regulated in melanoma infiltrating T lymphocytes (TILs) (see Dotti (2009) Blood 114 (8): 1457-58). Tumors have been found to express the PD1 ligand PD-L1 or, more rarely, the PD1 ligand PDL2 which, when combined with the up-regulation of PD1 in CTLs, may be a contributory factor in the loss in T-cell functionality and the inability of CTLs to mediate an effective anti-tumor response. Researchers have shown that in mice chronically infected with lymphocytic choriomeningitis virus (LCMV), administration of anti-PD1 antibodies blocked PD1-PDL interaction and was able to restore some T-cell functionality (proliferation and cytokine secretion), leading to a decrease in viral load (Barber et al (2006) Nature 439(9): 682-687). Additionally, a fully human PD-1 specific IgG4 monoclonal antibody has been tested in the clinic in an oncology setting on patients with a variety of disease backgrounds (advanced melanoma, renal cell carcinoma, non-small cell lung cancer, colorectal cancer or prostate cancer). Clinical activity was observed in melanoma, renal cell and non-small cell lung cancer patients and preliminary data suggested that detection of PD1 ligand expression by the tumor prior to treatment correlated with clinical outcome (see Wolfe (2012) Oncology Business Review, July; and Pardoll, ibid).

Another modulator of T-cell activity is the CTLA-4 receptor, and it is also considered an immunological checkpoint gene. Similar to the T-cell receptor co-stimulator CD28, CTLA-4 interacts with the CD80 and CD86 ligands on antigen presenting cells. But while interaction of these antigens with CD28 causes activation of T-cells, interaction of CD80 or CD86 with CTLA-4 antagonizes T-cell activation by interfering with IL-2 secretion and IL-2 receptor expression, and by inhibiting the expression of critical cell cycle components. CTLA-4 is not found on the surface of most resting T-cells, but is up-regulated transiently after T-cell activation. Thus, CTLA-4 is also involved in the balance of activating and inhibiting T-cell activity (see Attia et al. (2005) J Clin Oncol. 23(25): 6043-6053). Initial clinical studies involving the use of CTLA 4 antibodies in subjects with metastatic melanoma found regression of the disease (Attia, ibid), but later studies found that subject treated with the antibodies exhibited side effects of the therapy (immune-related adverse events: rashes, colitis, hepatitis etc.) that seemed to be related to a breaking of self-tolerance. Analysis of this data suggested that greater tumor regression as a result of the anti-CTLA4 antibody correlated directly with a greater severity of immune-related adverse events (Weber (2007) Oncologist 12(7): 864-872).

Chimeric Antigen Receptors (CARs) are molecules designed to target immune cells to specific molecular targets expressed on cell surfaces. In their most basic form, they are receptors introduced to a cell that couple a specificity domain expressed on the outside of the cell to signaling pathways on the inside of the cell such that when the specificity domain interacts with its target, the cell becomes activated. Often CARs are made from variants of T-cell receptors (TCRs) where a specificity domain such as a scFv or some type of receptor is fused to the signaling domain of a TCR. These constructs are then introduced into a T-cell allowing the T-cell to become activated in the presence of a cell expressing the target antigen, resulting in the attack on the targeted cell by the activated T-cell in a non-MHC dependent manner (see Chicaybam et al (2011) Int Rev

*Immunol* 30:294-311). Currently, tumor specific CARs targeting a variety of tumor antigens are being tested in the clinic for treatment of a variety of different cancers. Examples of these cancers and their antigens that are being targeted includes follicular lymphoma (CD20 or GD2), neuroblastoma (CD171), non-Hodgkin lymphoma (CD20), lymphoma (CD19), glioblastoma (IL13Rα2), chronic lymphocytic leukemia or CLL and acute lymphocytic leukemia or ALL (both CD19). Virus specific CARs have also been developed to attack cells harboring virus such as HIV. For example, a clinical trial was initiated using a CAR specific for Gp100 for treatment of HIV (Chicaybam, ibid).

Adoptive cell therapy (ACT) is a developing form of cancer therapy based on delivering tumor-specific immune cells to a patient in order for the delivered cells to attack and clear the patient's cancer. ACT often involves the use of tumor-infiltrating lymphocytes (TILs) which are T-cells that are isolated from a patient's own tumor masses and expanded ex vivo to re-infuse back into the patient. This approach has been promising in treating metastatic melanoma, where in one study, a long term response rate of >50% was observed (see for example, Rosenberg et al (2011) *Clin Canc Res* 17(13): 4550). TILs are a promising source of cells because they are a mixed set of the patient's own cells that have T-cell receptors (TCRs) specific for the Tumor associated antigens (TAAs) present on the tumor (Wu et al (2012) *Cancer J* 18(2):160). However, as stated above, TILs often are up-regulated for PD1 expression, presumably due to PDL expression in the tumors, resulting in a population of cells that can target a specific cancer cell and infiltrate a tumor, but then are unable to kill the cancerous cells. In vitro studies have shown a significant increase in TIL proliferation in response to their cognate tumor antigen in the presence of anti-PD1 antibodies as compared to stimulation in the absence of the anti-PD1 antibody (Wu et al, ibid).).

As useful as it is to develop a technology that will cause a T-cell to re-direct its attention to specific cells such as cancer cells, there remains the issue that these target cells often express PD-1 ligand. As such, the PD1-PD-L1/PD-L2 interaction enables the tumor to escape action by the CAR-targeted T-cell by deactivating the T-cells and increasing apoptosis and cell exhaustion. Additionally, the PD1-PDL interactions are also involved in the repression of the T-cell response to HIV, where increased expression of both PD1 and PDL leads to T-cell exhaustion. Induction of CTLA-4 expression on activated T-cells is also one of the first steps to damping the immune response, and thus a T-cell armed with a CAR might become inactive due to the engagement of this system designed to balance T-cell activation with T-cell inhibition.

Thus, there remains a need for PD1-targeted and/or CTLA-4 modulators, for example PD1 and/or CTLA-4-targeted nucleases or transcription repressors that can be used in research and therapeutic applications.

SUMMARY

The present disclosure relates to development of immunological checkpoint targeted nucleases, for example engineered meganucleases, CRISPR/Cas nuclease systems, zinc finger nucleases (ZFNs) and TALE-nucleases (TALENs) for inactivation of PD1 and/or CTLA-4, optionally in combination with engineered chimeric antigen receptors (CARs) and/or engineered T-cell receptors (TCRs), to prevent or reduce T-cell inhibition. This disclosure also relates to the development of transcription repressors, for example CRISPR/Cas-, zinc finger- and TALE-based fusion proteins for inactivation of PD1 and/or CTLA-4, optionally in combination with engineered chimeric antigen receptors (CARs) and/or engineered T-cell receptors (TCRs), to prevent or reduce T-cell inhibition.

The present disclosure provides zinc finger proteins specific for human and rodent PD1 and fusion proteins, including zinc finger protein transcription factors (ZFP-TFs) or zinc finger nucleases (ZFNs), comprising these PD1-specific zinc finger proteins. The disclosure also provides zinc finger proteins specific for human CTLA-4 and fusion proteins, including zinc finger nucleases (ZFNs), comprising these CTLA-4-specific zinc finger proteins. The disclosure also provides active TALE proteins specific for human PD1 and fusion proteins, including TALE nucleases (TALENs) comprising these PD1-specific TALE DNA binding domains. In certain embodiments, the zinc finger protein comprising five zinc finger recognition regions ordered from F1 to F5 from N-terminus to C-terminus, and wherein the recognition regions comprise the following amino acid sequences shown in a single row of Table 2a or Table 2c. In other embodiments, the TAL-effector domain (TALE) comprises a plurality of TALE repeat units, each repeat unit comprising an Repeat Variable Diresidue (RVD) region that binds to a nucleic acid in a target sequence, wherein the TALE binds to a target sequence as shown SEQ ID NO:29-34 (as shown in Table 5).

The proteins comprising PD1 and/or CTLA-4 specific zinc finger, CRISPR/Cas or TALE proteins of the invention may be used for research and therapeutic purposes, including for treatment of any disease or disorder in which PD1 is expressed (e.g., overexpressed), resulting in inactivation or depletion of activated T-cells due to overexpression of a PDL by a targeted cell and/or a disease or disorder in which prevention of CTLA-4 engagement will be beneficial. For example, a zinc finger, TALE and/or CRISPR/Cas nuclease targeting of the PD1 locus in T-cells can be used to block PD1-dependent immune suppression in both chronic infectious diseases and malignancies. Similarly, zinc finger, CRISPR/Cas TALE nuclease and/or targeting of CTLA-4 in T-cells can be used to prevent CTLA-4 mediated T-cell inhibition, for example in the treatment of cancer. Fusion proteins derived from a linkage of a TALE DNA binding domain and a meganuclease can also be directed to PD1 and/or CTLA-4 for a similar gene knock down or knock out. Transcriptional repressor proteins, derived from engineered zinc finger proteins, TALEs and CRISPR/Cas fused to transcription repressor domains can also be used to prevent PD1 or CTLA-4 mediated T-cell inhibition.

In another aspect of the invention, the fusion proteins comprise zinc finger (ZFN), CRISPR/Cas or TALE (TALEN) nucleases that are specific for the human PD1 or CTLA-4 genes. In certain embodiments, the zinc finger domains of the nuclease fusion proteins specific for PD-1 comprise the non-naturally occurring recognition helices and/or bind to the target sites disclosed in U.S. Patent Publication No. 20110136895 (see Tables 2a and 2b) and the TALE proteins bind to target sites in PD1 as shown in Tables 5a and 5b. In other embodiments, the zinc finger domains of the fusion proteins specific for CTLA-4 comprise the non-naturally occurring recognition helices shown in Table 2c and/or bind to the target sites shown in Table 3.

In another aspect, described herein is a CRISPR/Cas system that binds to target site in a region of interest in a PD1 or CTLA-4 gene in a genome, wherein the CRISPR/Cas system comprises a CRIPSR/Cas nuclease and an engineered crRNA/tracrRNA (or single guide RNA). See, also, U.S. Patent Publication No. 20150056705.

In another aspect, a polynucleotide encoding a nuclease as described herein is provided, for example a polynucleotides encoding one or more zinc finger nucleases (ZFNs), one or more TALENs, one or more meganucleases and/or one or more CRISPR/Case nucleases. The polynucleotide can comprise DNA, RNA or combinations thereof. In certain embodiments, the polynucleotide comprises a plasmid. In other embodiments, the polynucleotide encoding the nuclease comprises mRNA.

In one aspect, the methods and compositions of the invention comprise engineered (genetically modified) T-cells. T-cells include, but are not limited to, helper T-cells (e.g., CD4+ cells), cytotoxic T-cells (e.g., CD8+), memory T-cells, regulatory T-cells, tumor infiltrating lymphocytes (TILs, CD3+) and the like. In certain embodiments, the T-cells comprise a PD-1 specific nuclease (e.g., for inactivation of PD1 in the cell), while in further embodiments, the T-cells comprise a PD-1 specific nuclease and at least one transgene donor. In certain embodiments, the T-cells comprise a CTLA-4 specific nuclease (e.g., for inactivation of CTLA-4 in the cell), while in further embodiments, the T-cells comprise a CTLA-4 specific nuclease and at least one transgene donor. In other embodiments, the genetically modified T-cells are modified by a nuclease at both an endogenous PD1 gene and endogenous CTLA-4 gene. In still further embodiments, the genetically modified T-cells are modified by at least one nuclease at the endogenous TCR, and the endogenous PD1 and CTLA-4 genes. In some embodiments, the at least one transgene donor encodes a chimeric antibody receptor (CAR). In certain embodiments, the CAR donor is integrated into an endogenous PD1 and/or CTLA-4 gene. In some embodiments, the CAR donor is integrated by targeted integration into a safe harbor location. In other embodiments, the CAR-encoding exogenous sequence is introduced via random integration using a lentiviral delivery system. In other embodiments, the CAR donor is introduced via random integration using a transposon based delivery system.

In other embodiments, the T-cells comprise at least two transgene donors. In some embodiments, the at least two transgene donors encode subunits of a T-cell receptor (TCR), e.g. TRAC and TRBC (see United Stated Patent Publication No. 20110158957, incorporated by reference herein). In some instances, the TCR subunits, when expressed from the donors, comprise a TCR with specificity for a TAA. Some embodiments include engineered TCR chains designed to minimize association with an endogenous TCR. In other embodiments, the endogenous TCR is rendered non-functional via engineered nuclease mediated gene disruption.

In some embodiments, the transgene donor is inserted into the PD-1 and/or CTLA-4 locus, such that the transgene is expressed and PD1 or CTLA 4 expression is disrupted. In other embodiments, the engineered T-cells comprise the PD1 or CTLA-4 specific nuclease, a second nuclease specific for a safe harbor, and a transgene such that the transgene is inserted into a safe harbor locus (e.g. AAVS1, CCR5 or HPRT) by targeted integration. See, e.g., U.S. Pat. No. 7,951,925 and U.S. Publication Nos. 20080159996; 201000218264; 20130177983; 20130177960; 20130137104; and 20130122591. In other embodiments, the T-cells comprise a PD1 and/or CTLA-4 specific nuclease, a transgene encoding a CAR, and a second transgene encoding another open reading frame. In some embodiments, the second transgene encodes a suicide gene. In some embodiments, the T-cells comprise a PD1 and/or CTLA-4 specific nuclease, a transgene encoding a CAR and a set of transgenes encoding a TAA-specific TCR. In other aspects, the donor transgenes are integrated into the T-cells prior to the nucleases being integrated, while in some aspects, both the donor transgenes and the nucleases are introduced into the T-cell together.

In another aspect, described herein are methods of modifying a T-cell. In certain embodiments, PD1 and/or CTLA-4 expression in the T-cell is reduced or inactivated, for example using a zinc finger or TALE transcription factor, a zinc finger nuclease and/or a TALEN and/or CRIPSR/Cas system. In certain embodiments, the methods further comprise introducing one or more exogenous sequences (e.g., transgenes) into any of the PD1- and/or CTLA-4 modified cells as described herein, for example a transgene encoding a CAR and/or a set of transgenes encoding a TAA-specific TCR. In certain embodiments, the T-cell is activated, for example bead-activation as described in U.S. Publication No. 20080311095. In other embodiments, the T-cells are resting. In some aspects, the T-cell is a TIL. In other aspects, the T-cell comprises a T-cell line derived from a TIL. In some embodiments, the TIL is characterized for its HLA subtypes, and in other embodiments, the TILs carry specifically engineered HLA knock-outs and/or knock-ins (see US Patent Publication No. 20120060230, incorporated by reference herein).

In another aspect, the methods of the invention comprise a composition for therapeutic treatment of a subject in need thereof. In some embodiments, the composition comprises engineered T-cells or TILs comprising a PD1 or CTLA-4 specific nuclease, a safe harbor specific nuclease, at least one transgene donor encoding a CAR, a second transgene donor and any combinations of nucleases and donors thereof. In some aspects, the transgene donors encode a TAA-specific TCR. In other embodiments, the compositions comprise engineered T-cells or TILs comprising a PD1 or CTLA-4 specific nuclease and a transgene donor encoding a CAR.

In another aspect, provided herein are methods and compositions for the regulation of the PD1 or CTLA-4 gene. In certain embodiments, the methods comprise introducing a nuclease (e.g., ZFN, TALEN, CRISPR/Cas, meganuclease, TALE-meganuclease fusions, etc.) that binds to and modifies a PD1 or CTLA-4 gene. In certain embodiments, the nuclease is a fusion protein comprising a zinc finger or TALE fusion protein that is engineered to bind to a target site at the PD1 or CTLA-4 locus (or polynucleotide encoding the fusion protein) into cells from a subject with a disease or disorder to prevent or treat the disease or disorder. In some embodiments, the methods comprise introducing a transcription regulator (e.g., ZFP-TF, TALE-TF, CRIPSR/Cas-TF etc.) into a cell that binds to and represses expression of a PD1 or CTLA-4 gene. In some embodiments, the disease or disorder is a cancer or a malignancy, and the zinc finger or TALE fusion protein is a nuclease or a fusion protein comprising a transcription repression domain. In other embodiments, the nuclease comprises a CRISPR/Cas nuclease system. Non-limiting examples of cancers that can be treated and/or prevented include lung carcinomas, pancreatic cancers, liver cancers, melanomas, bone cancers, breast cancers, colorectal cancers, leukemias, ovarian cancers, lymphomas, brain cancers and the like.

A kit, comprising the ZFNs, TALENs and/or CRIPSR/Cas system of the invention, is also provided. The kit may comprise nucleic acids encoding the ZFNs, TALENs or CRISPR/Cas system, (e.g. RNA molecules or ZFP, TALEN or Cas9 encoding genes contained in a suitable expression vector) and engineered sg RNA if needed, or aliquots of the

DETAILED DESCRIPTION

Figure 1:
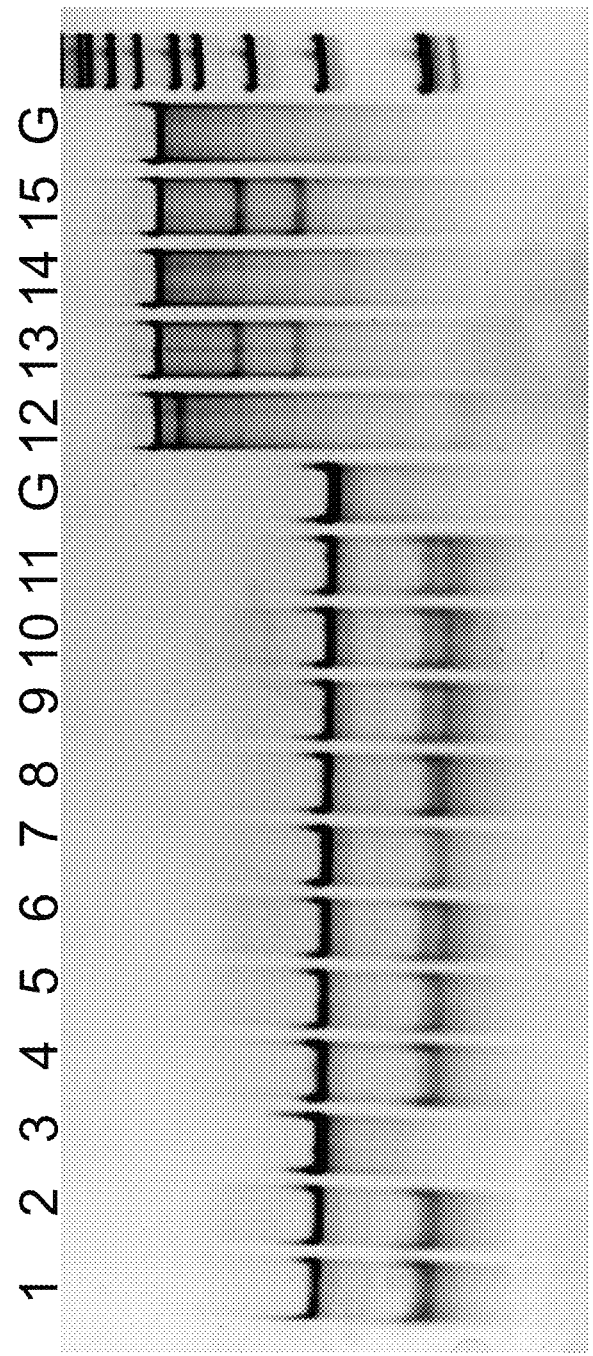
FIG. 1 depicts a gel showing the activity (as measured by % indel detection) of PD1-specific TALENs in K562 cells using the Cel-I assay (described in the text). Lane designations are as in text and % indels detected is indicated at the bottom of each lane.

Described herein are compositions and methods for modulation of PD1 and/or CTLA-4. These compositions and methods are useful for research and therapeutic applications and involve the use of genome editing via engineered nucleases to disrupt the PD1 and/or CTLA-4 gene. The inventive methods also include PD1 or CTLA-4 specific zinc finger or TALE DNA binding domain fused to transcription repressors to prevent expression of the PD1 or CTLA-4 genes. The methods and compositions included also describe the use of chimeric antigen receptors for activation of T-cells against specific cell targets in T-cells with a PD1 and/or CTLA-4 disruption.

Interaction of PD1, expressed on a T-cell, with PD1-ligand can cause deactivation of the T-cell. Some cancer cells express PD1 ligands, and in this way, are able to avoid immune surveillance and are able to proliferate despite the presence of T-cells that are capable, in the absence of PD-1 ligand, of destroying that cancer cell. Furthermore, even if the T-cell has been modified such that it expresses a CAR that activates and redirects that T-cell to a cell bearing a particular marker, expression of PD1 ligands by that targeted cell can cause desensitization of the activated T-cell, and the desensitized T-cell will then no longer act on the targeted cell.

CTLA-4 expression is induced upon T-cell activation on activated T-cells, and competes for binding with the antigen presenting cell activating antigens CD80 and CD86. Interaction of CTLA-4 with CD80 or CD86 causes T-cell inhibition and serves to maintain balance of the immune response. However, inhibition of the CTLA-4 interaction with CD80 or CD86 may prolong T-cell activation and thus increase the level of immune response to a cancer antigen. The present invention describes inhibition of the CTAL-4 interaction via a blockade of its expression with a zinc finger or TALE-transcription factor fusion, or via treatment of the T-cell with a CTLA-4 specific nuclease to knock out the gene.

CAR technology offers the potential for designer T-cells that will attack specific cells, where the target of those T-cells is chosen by the investigator. Medical researchers have long suggested that T-cells regularly remove malignant or aberrant cells as a matter of course, and yet there are some cancers that are able to escape, perhaps through the use of PD-1 ligand driven immune response damping. Thus, as promising as the use of CARs appears to be, the combination of T-cells engineered to express CARs (which targets them to particular tumor cells) in combination with transcription factors and/or nucleases (e.g., zinc finger, TALE, and/or CRISPR/Cas based) to repress or knock out PD1 or CTLA-4 expression in those same cells provides novel cell and animal models for, and methods of, researching and treating various diseases and disorders.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. Each TALE repeat unit includes 1 or 2 DNA-binding residues making up the Repeat Variable Diresidue (RVD), typically at positions 12 and/or 13 of the repeat. The natural (canonical) code for DNA recognition of these TALEs has been determined such that an HD sequence at positions 12 and 13 leads to a binding to cytosine (C), NG binds to T, NI to A, NN binds to G or A, and NG binds to T and non-canonical (atypical) RVDs are also known. See, U.S. Patent Publication No. 20110301073, incorporated by reference herein in its entirety.

A "CRISPR/Cas nuclease" or "CRISPR/Cas nuclease system" includes a non-coding RNA molecule (guide) RNA that binds to DNA and Cas proteins (Cas9) with nuclease functionality (e.g., two nuclease domains). See, e.g., U.S. Patent Publication No. 20150056705.

In any of the methods described herein, additional pairs of zinc-finger and/or TALEN proteins can be used for additional double-stranded cleavage of additional target sites within the cell. In addition, a CRISPR/Cas system may be used alone or in combination with ZFNs and/or TALENs to induce additional double strand breaks.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084 and U.S. Publication No. 20110301073.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 20050064474, 20070218528, 20080131962 and 20110201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value there between or there above), preferably between about 100 and 1,000 nucleotides in length (or any integer there between), more preferably between about 200 and 500 nucleotides in length. "Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

A "chronic infectious disease" is a disease caused by an infectious agent wherein the infection has persisted. Such a disease may include hepatitis (A, B, or C), herpes virus (e.g., VZV, HSV-1, HSV-6, HSV-II, CMV, and EBV), and HIV/AIDS. Non-viral examples may include chronic fungal diseases such Aspergillosis, Candidiasis, Coccidioidomycosis, and diseases associated with *Cryptococcus* and Histoplasmosis. None limiting examples of chronic bacterial infectious agents may be *Chlamydia pneumoniae, Listeria monocytogenes*, and *Mycobacterium tuberculosis*.

The term "autoimmune disease" refers to any disease or disorder in which the subject mounts a destructive immune response against its own tissues. Autoimmune disorders can affect almost every organ system in the subject (e.g., human), including, but not limited to, diseases of the nervous, gastrointestinal, and endocrine systems, as well as skin and other connective tissues, eyes, blood and blood vessels. Examples of autoimmune diseases include, but are not limited to Hashimoto's thyroiditis, Systemic lupus erythematosus, Sjogren's syndrome, Graves' disease, Scleroderma, Rheumatoid arthritis, Multiple sclerosis, Myasthenia gravis and Diabetes.

The term "cancer" as used herein is defined as a hyperproliferation of cells whose unique trait—loss of normal controls—results in unregulated growth, lack of differentiation, local tissue invasion, and metastasis. With respect to the inventive methods, the cancer can be any cancer, including any of acute lymphocytic cancer, acute myeloid leukemia, alveolar rhabdomyosarcoma, bladder cancer, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, Hodgkin lymphoma, hypopharynx cancer, kidney cancer, larynx cancer, leukemia, liquid tumors, liver cancer, lung cancer, lymphoma, malignant mesothelioma, mastocytoma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, ureter cancer, and urinary bladder cancer. As used herein, the term "tumor" refers to an abnormal growth of cells or tissues of the malignant type, unless otherwise specifically indicated and does not include a benign type tissue. The term "inhibits or inhibiting" as used herein means reducing growth/replication.

The term "immunological checkpoint gene" refers to any gene that is involved in an inhibitory process (e.g., feedback loop) that acts to regulate the amplitude of an immune response, for example an immune inhibitory feedback loop that mitigates uncontrolled propagation of harmful immune responses. These responses include contributing to a molecular shield that protects against collateral tissue damage that might occur during immune responses to infections and/or maintenance of peripheral self-tolerance. Non-limiting examples of immunological checkpoint genes include members of the extended CD28 family of receptors and their ligands as well as genes involved in co-inhibitory pathways (e.g., CTLA-4 and PD-1).

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain); fusion nucleic acids (for example, a nucleic acid encoding the fusion protein described supra) and fusions between nucleic acids and proteins (e.g., CRISPR/Cas nuclease system). Examples of the second type of fusion molecule include, but are not limited to, a fusion between a triplex-forming nucleic acid and a polypeptide, and a fusion between a minor groove binder and a nucleic acid.

Expression of a fusion molecule in a cell can result from delivery of the fusion molecule to the cell, for instance for fusion proteins by delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and/or polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the expression level of a gene. Modulation of expression can include, but is not limited to, gene activation and gene repression. Modulation may also be complete, i.e. wherein gene expression is totally inactivated or is activated to wildtype levels or beyond; or it may be partial, wherein gene expression is partially reduced, or partially activated to some fraction of wildtype levels. "Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE or CasDNA-binding domain is fused to a cleavage domain, the DNA-binding domain and the cleavage domain are in operative linkage if, in the fusion polypeptide, the DNA-binding domain portion is able to bind its target site and/or its binding site, while the cleavage domain is able to cleave DNA in the vicinity of the target site. Similarly, with respect to a fusion polypeptide in which a ZFP, TALE or CasDNA-binding domain is fused to an activation or repression domain, the DNA-binding domain and the activation or repression domain are in operative linkage if, in the fusion polypeptide, the DNA-binding domain portion is able to bind its target site and/or its binding site, while the activation domain is able to upregulate gene expression or the repression domain is able to downregulate gene expression. ZFPs fused to domains capable of regulating gene expression are collectively referred to as "ZFP-TFs" or "zinc finger transcription factors", while TALEs fused to domains capable of regulating gene expression are collectively referred to as "TALE-TFs" or "TALE transcription factors" and CRISPR/Cas proteins linked to domains capable of regulating gene expression are collectively referred to "CRISPR/Cas TFs".

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

A "chimeric antigen receptor" (CAR) is an artificially constructed hybrid protein or polypeptide comprising a specificity or recognition (i.e. binding) domain linked to an immune receptor responsible for signal transduction in lymphocytes. Most commonly, the binding domain is derived from a Fab antibody fragment that has been fashioned into a single chain scFv via the introduction of a flexible linker between the antibody chains within the specificity domain.

Other possible specificity domains can include the signaling portions of hormone or cytokine molecules, the extracellular domains of receptors, and peptide ligands or peptides isolated by library (e.g. phage) screening (see Ramos and Dotti, (2011) *Expert Opin Bio Ther* 11(7): 855). Flexibility between the signaling and the binding portions of the CAR may be a desirable characteristic to allow for more optimum interaction between the target and the binding domain, so often a hinge region is included. One example of a structure that can be used is the CH2-CH3 region from an immunoglobulin such as an IgG molecule. The signaling domain of the typical CAR comprises intracellular domains of the TCR-CD3 complex such as the zeta chain. Alternatively, the γ chain of an Fc receptor may be used. The transmembrane portion of the typical CAR can comprise transmembrane portions of proteins such as CD4, CD8 or CD28 (Ramos and Dotti, ibid). Characteristics of some CARs include their ability to redirect T-cell specificity and reactivity toward a selected target in a non-MHC-restricted manner. The non-MHC-restricted target recognition gives T-cells expressing CARs the ability to recognize a target independent of antigen processing, thus bypassing a major mechanism of tumor escape.

So called "first generation" CARs often comprise a single internal signaling domain such as the CD3 zeta chain, and are thought to be somewhat ineffectual in the clinic, perhaps due to incomplete activation. To increase performance of T-cells bearing these CARs, second generation CARs have been generated with the ability of proving the T-cell additional activation signals by including another stimulatory domain, often derived from the intercellular domains of other receptors such as CD28, CD134/OX40, CD137/4-1BB, Lck, ICOS and DAP10. Additionally, third generation CARs have also been developed wherein the CAR contains three or more stimulatory domains (Ramos and Dotti, ibid).

In some instances, CAR can comprise an extracellular hinge domain, transmembrane domain, and optionally, an intracellular hinge domain comprising CD8 and an intracellular T-cell receptor signaling domain comprising CD28, 4-1BB, and CD3.zeta. CD28 is a T-cell marker important in T-cell co-stimulation. CD8 is also a T-cell marker. 4-1BB transmits a potent costimulatory signal to T-cells, promoting differentiation and enhancing long-term survival of T lymphocytes. CD3.zeta. associates with TCRs to produce a signal and contains immunoreceptor tyrosine-based activation motifs (ITAMs). In other instances, CARs can comprise an extracellular hinge domain, transmembrane domain, and intracellular T-cell signaling domain comprising CD28 and CD3.zeta. In further instances, CARs can comprise an extracellular hinge domain and transmembrane domain comprising CD8 and an intracellular T-cell receptor signaling domain comprising CD28 and CD3.zeta.

Overview

Described herein are DNA-binding molecules (e.g., zinc finger, TALE and/or CRISPR/Cas nucleases and/or transcription factors targeted to the PD1 gene and/or CTLA-4 gene as well as compositions comprising and methods of using these nucleases and artificial transcription factors for treatment of disease or disorders, particularly disorders in which PD1 or PD1 ligands are undesirably expressed on cells of the immune system, cancers and/or autoimmune diseases and/or diseases or disorders in which repression of CTLA-4 expression would be beneficial. For treatment of a subject with a disease or disorder that is ameliorated by the modulation of the PD1/PD1 ligand interaction, or CTLA-4 mediated T-cell inhibition, the nucleases described herein can be introduced in vivo or ex vivo into cells (e.g., primary cells such as T-cells isolated from a subject afflicted with such a disease) to prevent expression of PD1 or CTLA-4 on the treated cells. Following nuclease treatment, the PD1 or CTLA-4 knock out T-cells may be reintroduced into the subject for use as a medicament in the treatment of a chronic infectious disease or cancer, or maybe be expanded prior to re-introduction. Alternatively, modulation of the PD1 or CTLA-4 loci may occur in vivo through introduction of the necessary nucleases or engineered transcription factors into a subject. Similarly, stem cells may be used that have been treated with the PD1- and/or CTLA-4 specific nucleases (e.g., ZFNs, CRISPR/Cas nuclease systems and/or TALENs). These cells can be infused into an afflicted subject for treatment of such a medical condition.

In some instances, the PD1 or CTLA-4 specific nucleases or transcription factors may be used in concert with chimeric antigen receptors. Thus, the invention contemplates, for example, methods in which a CAR that specifically targets a protein or non-protein tumor antigen is introduced into a T-cell such that the T-cell bearing such a CAR will become activated in the presence of the antigen. The use of a CAR in a cell that has also been, or will be, treated with PD1- and/or CTLA-4-specific nucleases or transcription factors, in which the PD1 or CTLA-4 gene(s) is(are) knocked out or otherwise similarly modulated, results in a T-cell expressing a CAR of interest that is resistant to the PD1 ligand produced by the cancer cell and thus is not subject to PD-1 mediated T-cell exhaustion and/or resistant to CTLA-4 mediated T-cell inhibition.

Numerous cancer antigens are known in the art and may be targeted by specific CARs. By way of non-limiting examples, see Table 1 for tumor associated antigens that may be targeted by CARs (see Ramos and Dotti, ibid, and Orentas et al (2012), *Front in Oncol* 2:1).

TABLE 1

Tumor associated antigens suitable for CAR targeting

| Tumor type | Antigen | Description |
| --- | --- | --- |
| Gastrointenstinal | EGP2/EpCam | Epithelial glycoprotein 2/Epithelial cell adhesion molecule |
| Gastrointenstinal | EGP40 | Epithelial glycoprotein 40 |
| Gastrointenstinal | TAG72/CA72-4 | Tumor associated glycoprotein 72/cancer antigen 72-4 |
| Glioblastoma | IL13Rα2 | Interleukin 13 receptor alpha-2 subunit |
| Kidney | G250/MN/CA IX | Carbonic anhydrase IX |
| Lymphoid malignancies | CD19 | |
| Lymphoid malignancies | CD52 | |
| Lymphoid malignancies | CD33 | |
| Lymphoid malignancies | CD20 | Membrane-spanning 4-domains subfamily A member 1 |
| Lymphoid malignancies | TSLPR (CRLF2) | |
| Lymphoid malignancies | CD22 | Sialic acid-binding Ig-like lectin 2 |

TABLE 1-continued

Tumor associated antigens suitable for CAR targeting

| Tumor type | Antigen | Description |
| --- | --- | --- |
| Lymphoid malignancies | CD30 | TNF receptor superfamily member 8 |
| Lymphoid malignancies | κ | Kappa light chain |
| Melanoma | GD3 | GD3-Ganglioside |
| Melanoma | HLA-A1 + MAGE-1 | Human leukocyte antigen A1 + Melanoma antigen 1 |
| Neuroblastoma/Neural tumors | CD171 | L1 cell adhesion molecule |
| Neuroblastoma/Neural tumors | ALK | Anaplastic lymphoma kinase |
| Neuroblastoma/Neural tumors | GD2 | GD2-Ganglioside |
| Neuroblastoma/Neural tumors | CD47 | |
| Neuroblastoma/Neural tumors | EGFRvIII | |
| Neuroblastoma/Neural tumors | NCAM | Neural cell adhesion molecule |
| Ovary | FBP/αFR | Folate binding protein/alpha folate receptor |
| Ovary | Le(Y) | Lewis-Y antigen |
| Ovary | MUC1 | Mucin 1 |
| Prostate | PSCA | Prostate stem cell antigen |
| Prostate | PSMA | Prostate-specific membrane antigen |
| Rhadbomyosarcoma | FGFR4 | Fibroblast growth factor receptor 4 |
| Rhadbomyosarcoma | FAR | Fetal acetylcholine receptor |
| Several solid tumors | CEA | Carcinoembryonic antigen |
| Several solid tumors | ERBB2/HER2 | Avian ertyroblastic leukemia viral oncogene homolog 2/Human epidermal growth factor receptor 2 |
| Several solid tumors | ERBB3 + ERBB4 | Avian erthroblastic leukemia viral oncogene homology 3 + 4 |
| Several solid tumors | Mesothelin | |
| Various tumors | CD44v6 | Hyaluronate receptor variant 6 |
| Various tumors | B7-H3 | Adhesion receptor |
| Various tumors | Glypican-3,5 | Cell surface peptidoglycan |
| Various tumors | ROR1 | |
| Various tumors | Survivin | Anti-apoptotic molecule |
| Various tumors | FOLR1 | α folate receptor |
| Various tumors | WT1 | Wilm's tumor antigen |
| Various tumors | CD70 | |
| Various tumors | VEGFR2/FLK/KDR | Vascular endothelial growth factor 2/Fetal liver kinase 1/Kinase domain insert |

Further, recombinant expression vectors, for example vectors including a suicide gene, or such gene may be introduced separately. As used herein, the term "suicide gene" refers to a gene that causes the cell expressing the suicide gene to die. The suicide gene can be a gene that confers sensitivity to an agent, e.g., a drug that acts upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine deaminase, purine nucleoside phosphorylase, and nitroreductase.

DNA-Binding Domains

Described herein are compositions comprising a DNA-binding domain that specifically binds to a target site in a PD1 or CTLA-4 locus. Any DNA-binding domain can be used in the compositions and methods disclosed herein, including but not limited to a zinc finger DNA-binding domain, a TALE DNA binding domain, CRISPR/Cas DNA-binding nuclease system or a DNA-binding domain from a meganuclease.

In certain embodiments, the DNA binding domain comprises a zinc finger protein or TALE DNA-binding protein. Preferably, the zinc finger protein is non-naturally occurring in that it is engineered to bind to a target site of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties. In other embodiments, the DNA binding domain comprises a TALE DNA binding domain (see, co-owned US Patent publication No. 20110301073, incorporated by reference in its entirety herein).

An engineered zinc finger or TALE DNA binding domain can have a novel binding specificity, compared to a naturally-occurring zinc finger or TALE protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos.

5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins or TALEs may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in co-owned WO 02/077227.

Selection of target sites; ZFPs or TALEs and methods for design and construction of fusion proteins (and polynucleotides encoding same) are known to those of skill in the art and described in detail in U.S. Pat. Nos. 6,140,081; 5,789, 538; 6,453,242; 6,534,261; 5,925,523; 6,007,988; 6,013, 453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, DNA-binding domains may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128.

In other embodiments, the DNA-binding domain is in a CRISPR/Cas nuclease system, guided by, for example, an RNA molecule.

In certain embodiments, the DNA binding domain is an engineered zinc finger protein that binds (in a sequence-specific manner) to a target site in a PD1 or CTLA-4 locus and modulates expression of PD1 or CTLA-4. PD1 and CTLA-4 target sites typically include at least one zinc finger but can include a plurality of zinc fingers (e.g., 2, 3, 4, 5, 6 or more fingers). Usually, the ZFPs include at least three fingers. Certain of the ZFPs include four, five or six fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, wherein these regulatory domains can be transcriptional activation or repression domains.

In other embodiments, the DNA-binding domain comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay et al (2007) *Science* 318:648-651). These proteins contain a DNA binding domain and a transcriptional activation domain. One of the most well characterized TALEs is AvrBs3 from *Xanthomonas campestris* pv. *Vesicatoria* (see Bonas et al (1989) *Mol Gen Genet* 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg1 1 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

The CRISPR/Cas System

Compelling evidence has recently emerged for the existence of an RNA-mediated genome defense pathway in archaea and many bacteria that has been hypothesized to parallel the eukaryotic RNAi pathway (for reviews, see Godde and Bickerton, 2006. *J. Mol. Evol.* 62: 718-729; Lillestol et al., 2006. *Archaea* 2: 59-72; Makarova et al., 2006. *Biol. Direct* 1: 7.; Sorek et al., 2008. *Nat. Rev. Microbiol.* 6: 181-186). Known as the CRISPR-Cas system or prokaryotic RNAi (pRNAi), the pathway is proposed to arise from two evolutionarily and often physically linked gene loci: the CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60). CRISPR loci in microbial hosts contain a combination of CRISPR-associated (Cas) genes as well as non-coding RNA elements capable of programming the specificity of the CRISPR-mediated nucleic acid cleavage. The individual Cas proteins do not share significant sequence similarity with protein components of the eukaryotic RNAi machinery, but have analogous predicted functions (e.g., RNA binding, nuclease, helicase, etc.) (Makarova et al., 2006. *Biol. Direct* 1: 7). The CRISPR-associated (cas) genes are often associated with CRISPR repeat-spacer arrays. More than forty different Cas protein families have been described. Of these protein families, Cas1 appears to be ubiquitous among different CRISPR/Cas systems. Particular combinations of cas genes and repeat structures have been used to define 8 CRISPR subtypes (Ecoli, Ypest, Nmeni, Dvulg, Tneap, Hmari, Apern, and Mtube), some of which are associated with an additional gene module encoding repeat-associated mysterious proteins (RAMPs). More than one CRISPR subtype may occur in a single genome. The sporadic distribution of the CRISPR/Cas subtypes suggests that the system is subject to horizontal gene transfer during microbial evolution.

There are three types of CRISPR/Cas systems which all incorporate RNAs and Cas proteins. Types I and III both have Cas endonucleases that process the pre-crRNAs, that, when fully processed into crRNAs, assemble a multi-Cas protein complex that is capable of cleaving nucleic acids that are complementary to the crRNA.

The Type II CRISPR (exemplified by Cas9) is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation,' (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system.

The primary products of the CRISPR loci appear to be short RNAs that contain the invader targeting sequences, and are termed guide RNAs or prokaryotic silencing RNAs (psiRNAs) based on their hypothesized role in the pathway (Makarova et al. (2006) *Biol. Direct* 1:7; Hale et al. (2008) *RNA* 14: 2572-2579). RNA analysis indicates that CRISPR locus transcripts are cleaved within the repeat sequences to release ~60- to 70-nt RNA intermediates that contain individual invader targeting sequences and flanking repeat fragments (Tang et al. (2002) *Proc. Natl. Acad. Sci.* 99: 7536-7541; Tang et al. (2005) *Mol. Microbiol.* 55:469-481; Lillestol et al. (2006) *Archaea* 2:59-72; Brouns et al. (2008) *Science* 321: 960-964; Hale et al. (2008) *RNA* 14:2572-2579). In the archaeon *Pyrococcusfuriosus*, these intermediate RNAs are further processed to abundant, stable ~35- to 45-nt mature psiRNAs (Hale et al. (2008) *RNA* 14: 2572-2579).

In type II CRISPR/Cas systems, crRNAs are produced using a different mechanism where a trans-activating RNA (tracrRNA) complementary to repeat sequences in the pre-crRNA, triggers processing by a double strand-specific RNase III in the presence of the Cas9 protein. Cas9 is then able to cleave a target DNA that is complementary to the mature crRNA however cleavage by Cas 9 is dependent both upon base-pairing between the crRNA and the target DNA, and on the presence of a short motif in the crRNA referred to as the PAM sequence (protospacer adjacent motif) (see Qi et al. (2013) *Cell* 152:1173). In addition, the tracrRNA must also be present as it base pairs with the crRNA at its 3' end, and this association triggers Cas9 activity.

The requirement of the crRNA-tracrRNA complex can be avoided by use of an engineered "single-guide RNA" (sgRNA) that comprises the hairpin normally formed by the annealing of the crRNA and the tracrRNA (see, Jinek et al. (2012) *Science* 337:816 and Cong et al. (2013) *Sciencexpress*/10.1126/science.1231143). In *S. pyrogenes*, the engineered tracrRNA:crRNA fusion, or the sgRNA, guides Cas9 to cleave the target DNA when a double strand RNA:DNA heterodimer forms between the Cas associated RNAs and the target DNA. This system comprising the Cas9 protein and an engineered sgRNA containing a PAM sequence has been used for RNA guided genome editing (see Ramalingam, ibid) and has been useful for zebrafish embryo genomic editing in vivo (see Hwang et al. (2013) *Nature Biotechnology* 31(3):227) with editing efficiencies similar to ZFNs and TALENs.

Cas Proteins

The Cas9 protein has at least two nuclease domains: one nuclease domain is similar to a HNH endonuclease, while the other resembles a Ruv endonuclease domain. The HNH-type domain appears to be responsible for cleaving the DNA strand that is complementary to the crRNA while the Ruv domain cleaves the non-complementary strand.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof.

"Cas polypeptide" encompasses a full-length Cas polypeptide, an enzymatically active fragment of a Cas polypeptide, and enzymatically active derivatives of a Cas polypeptide or fragment thereof. Suitable derivatives of a Cas polypeptide or a fragment thereof include but are not limited to mutants, fusions, covalent modifications of Cas protein or a fragment thereof.

Cas proteins and Cas polypeptides may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

The CRISPR/Cas system can also be used to inhibit gene expression. Lei et al. (2013) *Cell* 152(5):1173-1183) have shown that a catalytically dead Cas9 lacking endonuclease activity, when coexpressed with a guide RNA, generates a DNA recognition complex that can specifically interfere with transcriptional elongation, RNA polymerase binding, or transcription factor binding. This system, called CRISPR interference (CRISPRi), can efficiently repress expression of targeted genes.

Additionally, Cas proteins have been developed which comprise mutations in their cleavage domains to render them incapable of inducing a DSB, and instead introduce a nick into the target DNA ("Cas9 nicking enzyme", see Cong et al., ibid). In particular, the Cas nuclease comprises two nuclease domains, the HNH and RuvC-like, for cleaving the sense and the antisense strands of the target DNA, respectively. The Cas nuclease can thus be engineered such that only one of the nuclease domains is functional, thus creating a Cas nickase. See, e.g., Jinek et al., ibid, and Cong et al., ibid.

The Cas proteins of the invention may be mutated to alter functionality. Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

RNA Components of CRISPR/Cas

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see, Jinek, ibid and Cong, ibid).

Chimeric or sgRNAs can be engineered to comprise a sequence complementary to any desired target. The RNAs comprise 22 bases of complementarity to a target and of the form G[n19], followed by a protospacer-adjacent motif (PAM) of the form NGG. Thus, in one method, sgRNAs can be designed by utilization of a known ZFN target in a gene of interest by (i) aligning the recognition sequence of the ZFN heterodimer with the reference sequence of the relevant genome (human, mouse, or of a particular plant species); (ii) identifying the spacer region between the ZFN half-sites; (iii) identifying the location of the motif G[N20]GG that is closest to the spacer region (when more than one such motif overlaps the spacer, the motif that is centered relative to the spacer is chosen); (iv) using that motif as the core of the sgRNA. This method advantageously relies on proven nuclease targets. Alternatively, sgRNAs can be designed to target any region of interest simply by identifying a suitable target sequence that conforms to the G[n20]GG formula.

Target Sites

As described in detail above, DNA domains (ZFPs, TALEs, CRISPR RNAs, meganucleases) can be engineered to bind to any sequence of choice in a locus. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Publication No. 20110301073.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Selection of target sites; nucleases and methods for design and construction of fusion proteins (and polynucleotides encoding same) are known to those of skill in the art and described in detail in U.S. Patent Publication Nos. 20050064474 and 20060188987, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Publication No. 20110301073.

Donors

As noted above, insertion of an exogenous sequence (also called a "donor sequence" or "donor" or "transgene"), for example, for expression of a polypeptide, correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded or double-stranded and can be introduced into a cell in linear or circular form. See, e.g., U.S. Patent Publication Nos. 20100047805; 20110281361; 20110207221 and 20130326645. The donor sequence(s) can be contained within a DNA MC, which may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally inserted so that its expression is driven by the endogenous promoter at the integration site, namely the promoter that drives expression of the endogenous gene into which the donor is inserted (e.g., AAVS1, CCR5, HPRT etc. (see co-owned US patent U.S. Pat. Nos. 8,110,379 and 7,951,925, and U.S. Publication Nos. 20130137104 and 20130122591). However, it will be apparent that the donor may comprise a promoter and/or enhancer, for example a constitutive promoter or an inducible or tissue specific promoter.

Targeted insertion of non-coding nucleic acid sequence may also be achieved. Sequences encoding antisense RNAs, RNAi, shRNAs and micro RNAs (miRNAs) may also be used for targeted insertions.

The donor molecule may be inserted into an endogenous gene such that all, some or none of the endogenous gene is expressed. For example, a transgene as described herein may be inserted into an endogenous locus such that some (N-terminal and/or C-terminal to the transgene) or none of the endogenous sequences are expressed, for example as a fusion with the transgene. In other embodiments, the transgene (e.g., with or without additional coding sequences such as for the endogenous gene) is integrated into any endogenous locus, for example a safe-harbor locus. See, e.g., U.S. patent publications 20080299580; 20080159996 and 201000218264.

When endogenous sequences (endogenous or part of the transgene) are expressed with the transgene, the endogenous sequences may be full-length sequences (wild-type or mutant) or partial sequences. Preferably the endogenous sequences are functional. Non-limiting examples of the function of these full length or partial sequences include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

In certain embodiments, the exogenous sequence (donor) comprises a fusion of a protein of interest and, as its fusion partner, an extracellular domain of a membrane protein, causing the fusion protein to be located on the surface of the cell. In some instances, the donor encodes a CAR wherein the CAR encoding sequences are inserted into a safe harbor such that the CAR is expressed. In some instances, the CAR encoding sequences are inserted into a PD1 and/or a CTLA-4 locus. In other cases, the CAR is delivered to the cell in a lentivirus for random insertion while the PD1- or CTLA-4 specific nucleases are supplies as mRNAs. In some instances, the CAR is delivered via a viral vector system such as AAV or adenovirus along with mRNA encoding nucleases specific for a safe harbor (e.g. AAVS1, CCR5, albumin or HPRT). See, U.S. Patent Publication Nos. 20080299580; 20080159996; 201000218264; 20110301073; 20130177983 and 20130177960 and 20150056705. The cells can also be treated with mRNAs encoding PD1 and/or CTLA-4 specific nucleases. In certain embodiments, the polynucleotide encoding the CAR is supplied via a viral delivery system together with mRNA encoding HPRT specific nucleases and PD1- or CTLA-4 specific nucleases. Cells comprising an integrated CAR-encoding nucleotide at the HPRT locus can be selected for using 6-thioguanine, a guanine analog that can result in cell arrest and/or initiate apoptosis in cells with an intact HPRT gene. CARs that can be used with the methods and compositions of the invention include all types of these chimeric proteins, including first, second and third generation designs. CARS comprising specificity domains derived from antibodies are particularly useful, although specificity domains derived from receptors, ligands and engineered polypeptides are also envisioned by the invention. The intercellular signaling domains can be derived from TCR chains such as zeta and other members of the CD3 complex such as the γ and ε chains. In some cases, the CARs may comprise additional co-stimulatory domains such as the intercellular domains from CD28, CD137 (also known as 4-1BB) or CD134. In still further cases, two types of co-stimulator domains may be used simultaneously (i.e. CD3 zeta used with CD28+CD137).

Fusion Proteins

Fusion proteins comprising DNA-binding proteins (e.g., ZFPs or TALEs) as described herein and a heterologous regulatory (functional) domain (or functional fragment thereof) are also provided. Common domains include, e.g., transcription factor domains (activators, repressors, co-activators, co-repressors), silencers, oncogenes (e.g., myc, jun, fos, myb, max, mad, rel, ets, bel, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. U.S. Patent Publication Nos. 20050064474; 20060188987 and 2007/0218528 for details regarding fusions of DNA-binding domains and nuclease cleavage domains, incorporated by reference in their entireties herein.

Suitable domains for achieving activation include the HSV VP16 activation domain (see, e.g., Hagmann et al., *J. Virol.* 71, 5952-5962 (1997)) nuclear hormone receptors (see, e.g., Torchia et al., *Curr. Opin. Cell. Biol.* 10:373-383 (1998)); the p65 subunit of nuclear factor kappa B (Bitko & Barik, *J. Virol.* 72:5610-5618 (1998) and Doyle & Hunt, *Neuroreport* 8:2937-2942 (1997)); Liu et al., *Cancer Gene Ther.* 5:3-28 (1998)), or artificial chimeric functional domains such as VP64 (Beerli et al., (1998) *Proc. Natl. Acad. Sci. USA* 95:14623-33), and degron (Molinari et al., (1999) *EMBO J.* 18, 6439-6447). Additional exemplary activation domains include, Oct 1, Oct-2A, Sp 1, AP-2, and CTF1 (Seipel et al., *EMBO J.* 11, 4961-4968 (1992) as well as p300, CBP, PCAF, SRC1 PvALF, AtHD2A and ERF-2. See, for example, Robyr et al. (2000) *Mol. Endocrinol.* 14:329-347; Collingwood et al. (1999) *J Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

It will be clear to those of skill in the art that, in the formation of a fusion protein (or a nucleic acid encoding same) between a DNA-binding domain and a functional domain, either an activation domain or a molecule that interacts with an activation domain is suitable as a functional domain. Essentially any molecule capable of recruiting an activating complex and/or activating activity (such as, for example, histone acetylation) to the target gene is useful as an activating domain of a fusion protein. Insulator domains, localization domains, and chromatin remodeling proteins such as ISWI-containing domains and/or methyl binding domain proteins suitable for use as functional domains in fusion molecules are described, for example, in co-owned U.S. Patent Publications 2002/0115215 and 2003/0082552 and in co-owned WO 02/44376.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

Additional exemplary functional domains are disclosed, for example, in co-owned U.S. Pat. No. 6,534,261 and US Patent Publication No. 2002/0160940.

Functional domains that are regulated by exogenous small molecules or ligands may also be selected. For example, RheoSwitch® technology may be employed wherein a functional domain only assumes its active conformation in the presence of the external RheoChem™ ligand (see for example US 20090136465). Thus, the ZFP, TALE or Cas may be operably linked to the regulatable functional domain wherein the resultant activity of the ZFP-TF, TALE-TF or CRISPR/Cas TF is controlled by the external ligand.

Nucleases

In certain embodiments, the fusion protein comprises a DNA-binding binding domain and cleavage (nuclease) domain. As such, gene modification can be achieved using a nuclease, for example an engineered nuclease. Engineered nuclease technology is based on the engineering of naturally occurring DNA-binding proteins. The methods and compositions described herein are broadly applicable and may involve any nuclease of interest. Non-limiting examples of nucleases include meganucleases, TALENs, zinc finger nucleases, and CRISPR/Cas nuclease systems. The nuclease may comprise heterologous DNA-binding and cleavage domains (e.g., zinc finger nucleases; TALENs, meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site). For example, engineering of homing endonucleases with tailored DNA-binding specificities has been described, see, Chames et al. (2005) *Nucleic Acids Res* 33(20):e178; Arnould et al. (2006) *J. Mol. Biol.* 355:443-458 and Grizot et al (2009) *Nucleic Acids Res* July 7 e publication. In addition, engineering of ZFPs has also been described. See, e.g., U.S. Pat. Nos. 6,534,261; 6,607,882; 6,824,978; 6,979,539; 6,933,113; 7,163,824; and 7,013,219. The nuclease may comprise combinations of nucleic acid and protein (e.g., CRISPR/Cas).

In certain embodiment, the nuclease is a meganuclease (homing endonuclease). Naturally-occurring meganucleases recognize 15-40 base-pair cleavage sites and are commonly grouped into four families: the LAGLIDADG (SEQ ID NO: 121) family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J Mol. Biol.* 263:163-180; Argast et al. (1998) *J. Mol. Biol.* 280:345-353 and the New England Biolabs catalogue.

DNA-binding domains from naturally-occurring meganucleases, primarily from the LAGLIDADG (SEQ ID NO: 121) family, have been used to promote site-specific genome modification in plants, yeast, *Drosophila*, mammalian cells and mice, but this approach has been limited to the modification of either homologous genes that conserve the meganuclease recognition sequence (Monet et al. (1999), *Biochem. Biophysics. Res. Common.* 255: 88-93) or to pre-engineered genomes into which a recognition sequence has been introduced (Route et al. (1994), *Mol. Cell. Biol.* 14: 8096-106; Chilton et al. (2003), *Plant Physiology.* 133: 956-65; Puchta et al. (1996), *Proc. Natl. Acad. Sci. USA* 93: 5055-60; Rong et al. (2002), *Genes Dev.* 16: 1568-81; Gouble et al. (2006), *J. Gene Med.* 8(5):616-622). Accordingly, attempts have been made to engineer meganucleases to exhibit novel binding specificity at medically or biotechnologically relevant sites (Porteus et al. (2005), *Nat. Biotechnol.* 23: 967-73; Sussman et al. (2004), *J Mol. Biol.* 342: 31-41; Epinat et al. (2003), *Nucleic Acids Res.* 31: 2952-62; Chevalier et al. (2002) *Molec. Cell* 10:895-905; Epinat et al. (2003) *Nucleic Acids Res.*31:2952-2962; Ashworth et al. (2006) *Nature* 441:656-659; Paques et al. (2007) *Current Gene Therapy* 7:49-66; U.S. Patent Publication Nos. 20070117128; 20060206949; 20060153826; 20060078552; and 20040002092). In addition, naturally-occurring or engineered DNA-binding domains from meganucleases have also been operably linked with a cleavage domain from a heterologous nuclease (e.g., FokI).

In other embodiments, the nuclease is a zinc finger nuclease (ZFN). ZFNs comprise a zinc finger protein that has been engineered to bind to a target site in a gene of choice and cleavage domain or a cleavage half-domain.

As noted above, zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19: 656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; ZFNs and methods for design and construction of fusion proteins (and polynucleotides encoding same) are known to those of skill in the art and described in detail in U.S. Patent Publication Nos. 20050064474 and 20060188987, incorporated by reference in their entireties herein.

In addition, as disclosed in these and other references, zinc finger domains and/or multi-fingered zinc finger proteins may be linked together using any suitable linker sequences, including for example, linkers of 5 or more amino acids in length. See, e.g., U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In some embodiments, the nuclease is an engineered TALEN. Methods and compositions for engineering these proteins for robust, site specific interaction with the target sequence of the user's choosing have been published (see co-owned US patent Publication No. 20110301073).

In other embodiments, the nuclease is a CRISPR/Cas nuclease system as described herein.

Nucleases such as ZFNs, TALENs, CRISPR/Cas and/or meganucleases also comprise a nuclease (cleavage domain, cleavage half-domain). As noted above, the cleavage domain may be homologous or heterologous to the DNA-binding domain. For example, cleavage domains can include Cas nucleases (in a CRISPR/Cas system) or meganuclease cleavage domains with a meganuclease DNA-binding domain. Alternatively, heterologous cleavage domains include fusions proteins comprising zinc finger or TALE DNA-binding domain and a cleavage domain from a nuclease or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31, 978-982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95:10,570-10,575. Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using zinc finger-Fok I or TALE-FokI fusions, two fusion proteins, each comprising a FokI cleavage half-domain, can be used to reconstitute a catalytically active cleavage domain. Alternatively, a single polypeptide molecule containing a zinc finger or TALE DNA binding domain and two Fok I cleavage half-domains can also be used. Parameters for targeted cleavage and targeted sequence alteration using zinc finger- or TALE-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Exemplary engineered cleavage half-domains of FokI that form obligate heterodimers include a pair in which a first cleavage half-domain includes mutations at amino acid residues at positions 490 and 538 of FokI and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., Example 1 of co-owned U.S. Patent publication No. 20080131962, and issued U.S. Pat. No. 7,914,796, the disclosures of which are incorporated by reference in their entirety for all purposes.

In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild-type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See, U.S. Patent Publication No. 20110201055). Engineered cleavage half-domains described herein can be prepared using any suitable method, for example, by site-directed mutagenesis of wild-type cleavage half-domains (Fok I) as described in U.S. Patent Publication Nos. 20050064474; 20080131962; and 20110201055.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Engineered cleavage half-domains described herein can be prepared using any suitable method, for example, by site-directed mutagenesis of wild-type cleavage half-domains (Fok I) in U.S. Patent Publication Nos. 20050064474; 2009/0305346; 2008/0131962; and 20110201055.

Nuclease expression constructs can be readily designed using methods known in the art. See, e.g., United States Patent Publications 20030232410; 20050208489; 20050026157; 20050064474; 20060188987; 20060063231; and International Publication WO 07/014275. In certain embodiments, expression of the nuclease is under the control of an inducible promoter, for example the galactokinase promoter which is activated (de-repressed) in the presence of raffinose and/or galactose and repressed in presence of glucose. In particular, the galactokinase promoter is induced and the nuclease(s) expressed upon successive changes in the carbon source (e.g., from glucose to raffinose to galactose). Other non-limiting examples of inducible promoters include CUP1, MET15, PHO5, and tet-responsive promoters.

Nucleases that generate single-stranded breaks can also be used. In certain embodiments, a catalytically inactive nuclease is used in combination with a catalytically active nuclease to generate a single-stranded break (also referred to as "nickases"). Such nickases are described, for example, in U.S. Patent Publication No. 20100047805; Jinek et al, ibid; Cong et al., ibid. Nickases can be generated by specific mutation of amino acids in the catalytic domain of the enzyme, or by truncation of part or all of the domain such that it is no longer functional. Thus, in nucleases comprising two nuclease (cleavage) domains (e.g., ZFNs, TALENs, and CRISPR/Cas nuclease systems), this approach may be taken on either domain. Furthermore, a double strand break can be achieved in the target DNA by the use of two such single-stranded nickases. Each nickase cleaves one strand of the DNA and the use of two or more nickases can create a double strand break (e.g., a staggered double-stranded break) in a target double-stranded sequence.

Delivery

The nucleases and transcription factors, polynucleotides encoding same, and/or any donor polynucleotides and compositions comprising the proteins and/or polynucleotides described herein may be delivered to a target cell by any suitable means.

Suitable cells include but not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NSO, SP2/0-Ag14, HeLa, HEK293 (e.g., HEK293-F, HEK293-H, HEK293-T), and perC6 cells as well as insect cells such as *Spodoptera frugiperda* (Sf), or fungal cells such as *Saccharomyces, Pichia* and *Schizosaccharomyces*. In certain embodiments, the cell line is a CHO-K1, MDCK or HEK293 cell line. Suitable primary cells include peripheral blood mononuclear cells (PBMC), and other blood cell subsets such as, but not limited to, any T-cell, such as CD4+ T-cells, CD8+ T-cells, tumor infiltrating cells (TILs) or any other type of T-cell. Suitable cells also include stem cells such as, by way of example, embryonic stem cells, induced pluripotent stem cells, hematopoietic stem cells, neuronal stem cells and mesenchymal stem cells.

Methods of delivering transcription factors and nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

The transcription factors and nucleases as described herein may also be delivered using vectors, for example containing sequences encoding one or more of the proteins. Donor encoding polynucleotides may be similarly delivered. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more transcription factor and/or nuclease. Thus, when one or more ZFPs, TALEs, CRISPR/Cas molecules and/or donors are introduced into the cell, the ZFPs, TALEs, CRISPR/Cas molecules and/or donors may be carried on the same vector or on different vectors. When multiple vectors are used, each vector may comprise a sequence encoding one or multiple ZFPs, TALEs, CRISPR/Cas molecules and/or donors.

Conventional viral and non-viral based gene transfer methods can be used to introduce nucleic acids encoding engineered ZFPs, CRISPR/Cas molecules, TALEs and/or donors in cells (e.g., mammalian cells) and target tissues. Such methods can also be used to administer nucleic acids encoding ZFPs, TALES, CRISPR/Cas molecules, and/or donors to cells in vitro. In certain embodiments, nucleic acids encoding ZFPs, TALEs, CRISPR/Cas molecules, and/or donors are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel&Felgner, *TIBTECH* 11:211-217 (1993); Mitani&Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology*, Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, mRNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa® Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7) p. 643).

The use of RNA or DNA viral based systems for the delivery of nucleic acids encoding engineered ZFPs, TALEs, CRISPR/Cas molecules, and/or donors take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.*

66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors is described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type virus. The vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6 and AAV8, AAV 8.2, AAV9, and AAV rh10 and pseudotyped AAV such as AAV2/8, AAV2/5 and AAV2/6 can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, AAV, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additionally, AAV can be produced at clinical scale using baculovirus systems (see U.S. Pat. No. 7,479,554.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., Culture of Animal Cells, *A Manual of Basic Technique* (3rd ed. 1994)) and the references cited therein for a discussion of how to isolate and culture cells from patients).

Suitable cells include but not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NSO, SP2/0-Ag14, HeLa, HEK293 (e.g., HEK293-F, HEK293-H, HEK293-T), and perC6 cells as well as insect cells such as *Spodoptera frugiperda* (Sf), or fungal cells such as *Saccharomyces, Pichia* and *Schizosaccharomyces*. In certain embodiments, the cell line is a CHO-K1, MDCK or HEK293 cell line. Additionally, primary cells may be isolated and used ex vivo for reintroduction into the subject to be treated following treatment with the transcription factors and/or nucleases described herein. Suitable primary cells include peripheral blood mononuclear cells (PBMC), and other blood cell subsets such as, but not limited to, T-cells such as tumor infiltrating cells (TILs), CD4+ T-cells or CD8+ T-cells. Suitable cells also include stem cells such as, by way of example, embryonic stem cells, induced pluripotent stem cells, hematopoietic stem cells, neuronal stem cells and mesenchymal stem cells.

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see, Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T-cells), CD45+ (panBcells), GR-1 (granulocytes), and Tad (differentiated antigen presenting cells) (see, Inaba et al., *J. Exp. Med.* 176:1693-1702 (1992)).

Stem cells that have been modified may also be used in some embodiments. For example, stem cells that have been made resistant to apoptosis may be used as therapeutic compositions where the stem cells also contain the ZFPs, TALEs, CRISPR/Cas molecules and/or donors of the invention. Resistance to apoptosis may come about, for example, by knocking out BAX and/or BAK using BAX- or BAK-specific ZFNs (see, U.S. Pat. No. 8,597,912) in the stem cells, or those that are disrupted in a caspase, again using caspase-6 specific ZFNs for example.

Vectors (e.g., retroviruses, adenoviruses, liposomes, etc.) containing therapeutic ZFP, TALE, CRISPR/Cas molecules and/or donor nucleic acids can also be administered directly to an organism for transduction of cells in vivo. Alternatively, naked DNA or mRNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

Applications

The disclosed compositions and methods can be used for any application in which it is desired to modulate the expression of PD-land/or CTLA-4. In particular, these methods and compositions can be used where modulation of PD-1 or CTLA-4 is desired, including but not limited to, therapeutic and research applications. The invention also contemplates insertion of DNA sequences encoding a CAR and/or an engineered TCR into the genome of the PD-1 and/or CTLA-4 modulated cells (e.g., cells in which PD1 and/or CTLA-4 expression is modified via an engineered transcription factor or is knocked out using engineered nucleases). In some instances, the cells are TILs or cells expanded from TILs. The methods and compositions may be used to treat various disease and disorders including chronic infectious diseases such as HIV/AIDS and HCV and/or cancers (e.g., melanoma, ovarian cancer, colorectal/colon cancer, renal cell carcinoma, plasmacytoma/myeloma, breast cancer and lung cancer).

These and other diseases may also be treated with PD1- or CTLA-4 targeting nucleases or transcription factors in combination with CARs wherein the CARs are introduced into the cell via a viral delivery system. In some cases, an engineered TCR is also introduced into the cell, or may be introduced into the cell instead of a CAR. To facilitate operation of the engineered TCR, the endogenous TCR may also be disrupted.

Methods and compositions comprising PD1- or CTLA-4 specific nucleases or transcription factors may also be used in conjunction with other therapeutics designed to treat a chronic infectious disease or cancer. The nucleases as described herein (e.g., ZFNs, TALENs, CRISPR/Cas systems or polynucleotides encoding these molecules) or transcription factors (or polynucleotides encoding them) may be administered concurrently (e.g., in the same pharmaceutical compositions) or may be administered sequentially in any order. Any type of cancer can be treated, including, but not limited to lung carcinomas, pancreatic cancers, liver cancers, bone cancers, breast cancers, colorectal cancers, ovarian cancers, leukemias, melanomas, lymphomas, brain cancers and the like.

The PD1 and/or CTLA-4 specific nucleases or transcription factors may be used in conjunction with a CAR T-cell targeting system. The CARs may have specificity for a tumor antigen where the CAR specificity domain is a ScFv. Alternatively, CARs may be specific for a tumor antigen where the CAR specificity domain comprises a ligand or polypeptide. Non-limiting exemplary CARs include those targeted to CD33 (see Dutour et al, (2012) *Adv Hematol* 2012; 2012:683065), GD2 (Louis et al (2011) *Blood* 118 (23):650-6), CD19 (Savoldo et al, (2011) *J Clin Invest* 121(5): 1822 and Torikai et al (2012) *Blood* 119(24): 5697), IL-11Rα (Huang et al, (2012) *Cancer Res* 72(1):271-81), CD20 (Till et al (2012) *Blood* 119(17):3940-50), NY-ESO-1 (Schuberth et al, (2012) *Gene Ther* doi:10.1038/gt2012.48), ErbB2 (Zhao et al, (2009) *J. Immunol* 183(9): 5563-74), CD70 (Shaffer et al (2011) *Blood* 116(16):4304-4314), CD38 (Bhattacharayya et al (2012) *Blood Canc J* 2(6) p. e75), CD22 (Haso et al. (2012) *Canc Res* 72(8) S1, doi: 1158/1158-7445 AM2012-3504), CD74 (Stein et al (2004) *Blood* 104:3705-3711), CAIX (Lamers et al, (2011) *Blood* 117(1): 72-82) STEAP1 (see Kiessling et al. (2012) *Cancers* 4:193-217 for review of target) VEGF-R2 (U.S. Patent Publication No. US20120213783A1), the folate receptor (PCT patent publication WO2012099973) and IL-13 Rα (U.S. Pat. No. 7,514,537). In some cases, the CAR may be bi-specific (see US Patent publication No. US2001012967). In some cases, the T-cells are TILs. Additionally, the PD1 and/or CTLA-4 specific nucleases or transcription factors may be used in conjunction with a T cell or TIL comprising an engineered TCR.

The methods and compositions of the invention are also useful for the design and implementation of in vitro and in vivo models, for example, animal models of chronic infection, cancer or autoimmunity, which allows for the study of these disorders and furthers discovery of useful therapeutics. In some cases, the methods of the invention are useful for producing engineered T-cells that may be used in patients in need thereof. For some treatments, the patients are pre-treated with agents for partial or full myoablation prior to infusion of the T-cells.

The following Examples relate to exemplary embodiments of the present disclosure in which the nuclease comprises a ZFN or TALEN. It will be appreciated that this is for purposes of exemplification only and that other nucleases can be used, for instance CRISPR/Cas nuclease systems, homing endonucleases (meganucleases) with engineered DNA-binding domains and/or fusions of naturally occurring of engineered homing endonucleases (meganucleases) DNA-binding domains and heterologous cleavage domains.

EXAMPLES

Example 1: Identification of Persistently Biologically Active PD1- or CTLA-4 Specific ZFNs ZFNs were assembled against the human PD1 or CTLA-4 genes and were tested by ELISA and CEL1 assays as described in Miller et al. (2007) *Nat. Biotechnol.* 25:778-785 and U.S. Patent Publication No. 20050064474 and International Patent Publication WO2005/014791.

Specific examples of PD1-targeted ZFPs are disclosed in U.S. Patent Publication No. 20110136895 and shown in Table 2a and 2b and CTLA-4-targeted ZFP designs are shown in Table 2c. The first column in this table is an internal reference name (number) for a ZFP. "F" refers to the finger and the number following "F" refers to which zinc finger (e.g., "F1" refers to finger 1). The target sites for these CTLA-4 specific ZFNs are shown in Table 3.

TABLE 2a

Human PD1-targeted zinc finger proteins

| SBS # | Design | | | | | |
|---|---|---|---|---|---|---|
| | F1 | F2 | F3 | F4 | F5 | F6 |
| 12942 | QSGHLSR (SEQ ID NO: 34) | RSDSLSV (SEQ ID NO: 35) | HNDSRKN (SEQ ID NO: 36) | RSDDLTR (SEQ ID NO: 37) | RSDHLTQ (SEQ ID NO: 38) | N/A |
| 12946 | RSAALSR (SEQ ID NO: 39) | RSDDLTR (SEQ ID NO: 37) | RSDHLTT (SEQ ID NO: 40) | DRSALSR (SEQ ID NO: 6) | DRSALAR (SEQ ID NO: 41) | N/A |
| 12947 | RSAALAR (SEQ ID NO: 42) | RSDDLSK (SEQ ID NO: 3) | RNDHRKN (SEQ ID NO: 43) | DRSALSR (SEQ ID NO: 6) | DRSALAR (SEQ ID NO: 41) | N/A |
| 12934 | RSDHLSE (SEQ ID NO: 44) | TSSDRTK (SEQ ID NO: 45) | RSDHLSE (SEQ ID NO: 44) | QSASRKN (SEQ ID NO: 46) | N/A | N/A |
| 12971 | RSDVLSE (SEQ ID NO: 47) | RSANLTR (SEQ ID NO: 48) | RSDHLSQ (SEQ ID NO: 49) | TSSNRKT (SEQ ID NO: 50) | DRSNLSR (SEQ ID NO: 9) | RSDALAR (SEQ ID NO: 7) |
| 12972 | DDWNLSQ (SEQ ID NO: 51) | RSANLTR (SEQ ID NO: 48) | RSDHLSQ (SEQ ID NO: 49) | TSSNRKT (SEQ ID NO: 50) | DRSNLSR (SEQ ID NO: 9) | RSDALAR (SEQ ID NO: 7) |
| 18759 | RSSALSR (SEQ ID NO: 52) | RPLALKH (SEQ ID NO: 53) | RNDHRKN (SEQ ID NO: 43) | TRPVLKR (SEQ ID NO: 54) | DRSALAR (SEQ ID NO: 41) | N/A |
| 22237 | QSGHLSR (SEQ ID NO: 34) | RSDSLSV (SEQ ID NO: 35) | HNDSRKN (SEQ ID NO: 36) | RANSLLR (SEQ ID NO: 55) | RSDHLTQ (SEQ ID NO: 38) | N/A |

TABLE 2a-continued

Human PD1-targeted zinc finger proteins

Design

| SBS # | F1 | F2 | F3 | F4 | F5 | F6 |
|---|---|---|---|---|---|---|
| 25005 | RPSTLHR (SEQ ID NO: 56) | RSDELTR (SEQ ID NO: 57) | RNNNLRT (SEQ ID NO: 58) | TRPVLKR (SEQ ID NO: 54) | DRSALAR (SEQ ID NO: 41) | N/A |
| 25006 | RPSTLHR (SEQ ID NO: 56) | RSDELTR (SEQ ID NO: 57) | TNWHLRT (SEQ ID NO: 59) | TRPVLKR (SEQ ID NO: 54) | DRSALAR (SEQ ID NO: 41) | N/A |
| 25010 | RPSTLHR (SEQ ID NO: 56) | RSDELTR (SEQ ID NO: 57) | RTPHLTL (SEQ ID NO: 60) | TRPVLKR (SEQ ID NO: 54) | DRSALAR (SEQ ID NO: 41) | N/A |
| 25011 | RPSTLHR (SEQ ID NO: 56) | RSDELTR (SEQ ID NO: 57) | RSAQLAT (SEQ ID NO: 61) | TRPVLKR (SEQ ID NO: 54) | DRSALAR (SEQ ID NO: 41) | N/A |
| 25012 | RPSTLHR (SEQ ID NO: 56) | RSDELTR (SEQ ID NO: 57) | RCTHLYL (SEQ ID NO: 62) | TRPVLKR (SEQ ID NO: 54) | DRSALAR (SEQ ID NO: 41) | N/A |
| 25013 | RPSTLHR (SEQ ID NO: 56) | RSDELTR (SEQ ID NO: 57) | RPTQRYS (SEQ ID NO: 63) | TRPVLKR (SEQ ID NO: 54) | DRSALAR (SEQ ID NO: 41) | N/A |
| 25014 | RPSTLHR (SEQ ID NO: 56) | RSDELTR (SEQ ID NO: 57) | RANHREC (SEQ ID NO: 64) | TRPVLKR (SEQ ID NO: 54) | DRSALAR (SEQ ID NO: 41) | N/A |
| 25015 | RPSTLHR (SEQ ID NO: 56) | RSDELTR (SEQ ID NO: 57) | RANHREC (SEQ ID NO: 64) | TRPVLKR (SEQ ID NO: 54) | DRSALAR (SEQ ID NO: 41) | N/A |
| 25016 | RKFARPS (SEQ ID NO: 65) | RNFSRSD (SEQ ID NO: 66) | HPHHRMC (SEQ ID NO: 67) | TRPVLKR (SEQ ID NO: 54) | DRSALAR (SEQ ID NO: 41) | N/A |
| 25017 | RPSTLHR (SEQ ID NO: 56) | RSDELTR (SEQ ID NO: 57) | RMGRLST (SEQ ID NO: 68) | TRPVLKR (SEQ ID NO: 54) | DRSALAR (SEQ ID NO: 41) | N/A |
| 25022 | RPSTLHR (SEQ ID NO: 56) | RSDELTR (SEQ ID NO: 57) | RHSRLTT (SEQ ID NO: 69) | TRPVLMR (SEQ ID NO: 70) | DRSALAR (SEQ ID NO: 41) | N/A |
| 25023 | RPSTLHR (SEQ ID NO: 56) | RSDELTR (SEQ ID NO: 57) | RANHRVC (SEQ ID NO: 71) | TRPVLKR (SEQ ID NO: 54) | DRSALAR (SEQ ID NO: 41) | N/A |
| 25025 | RPSTLHR (SEQ ID NO: 56) | RSDELTR (SEQ ID NO: 57) | RSTHLLG (SEQ ID NO: 72) | TRPVLKR (SEQ ID NO: 54) | DRSALAR (SEQ ID NO: 41) | N/A |
| 25027 | RNAALTR (SEQ ID NO: 73) | RSDELTR (SEQ ID NO: 57) | RSCGLWS (SEQ ID NO: 74) | TRPVLKR (SEQ ID NO: 54) | DRSALAR (SEQ ID NO: 41) | N/A |
| 25028 | CNAALTR (SEQ ID NO: 75) | RSDELTR (SEQ ID NO: 57) | REEHRAT (SEQ ID NO: 76) | TRPVLKR (SEQ ID NO: 54) | DRSALAR (SEQ ID NO: 41) | N/A |
| 25029 | RNAALTR (SEQ ID NO: 73) | RSDELTR (SEQ ID NO: 57) | RHHHLAA (SEQ ID NO: 77) | TRPVLKR (SEQ ID NO: 54) | DRSALAR (SEQ ID NO: 41) | N/A |
| 25030 | RNAALTR (SEQ ID NO: 73) | RSDELTR (SEQ ID NO: 57) | RPMHLTN (SEQ ID NO: 78) | TRPVLKR (SEQ ID NO: 54) | DRSALAR (SEQ ID NO: 41) | N/A |
| 25031 | RNAALTR (SEQ ID NO: 73) | RSDELTR (SEQ ID NO: 57) | RSPHLYH (SEQ ID NO: 79) | TRPVLKR (SEQ ID NO: 54) | DRSALAR (SEQ ID NO: 41) | N/A |

TABLE 2a-continued

Human PD1-targeted zinc finger proteins

| SBS # | F1 | F2 | F3 | F4 | F5 | F6 |
|---|---|---|---|---|---|---|
| 25032 | RNAALTR (SEQ ID NO: 73) | RSDELTR (SEQ ID NO: 57) | RCEALFIH (SEQ ID NO: 80) | TRPVLKR (SEQ ID NO: 54) | DRSAQAR (SEQ ID NO: 81) | N/A |
| 25034 | RNAALTR (SEQ ID NO: 73) | RSDELTR (SEQ ID NO: 57) | RCEALFIH (SEQ ID NO: 80) | TRPVLKR (SEQ ID NO: 54) | DRSALAR (SEQ ID NO: 41) | N/A |
| 25036 | RNAALTR (SEQ ID NO: 73) | RSDELTR (SEQ ID NO: 57) | RSPHLYH (SEQ ID NO: 79) | TRPVLKR (SEQ ID NO: 54) | DRSALAR (SEQ ID NO: 41) | N/A |
| 25040 | RNAALTR (SEQ ID NO: 73) | RSDELTR (SEQ ID NO: 57) | RLPALLS (SEQ ID NO: 82) | TRPVLKR (SEQ ID NO: 54) | DRSALAR (SEQ ID NO: 41) | N/A |
| 25041 | HNAALTR (SEQ ID NO: 83) | RSDELTR (SEQ ID NO: 57) | RTYNRTQ (SEQ ID NO: 84) | TRPVLKR (SEQ ID NO: 54) | DRSALAR (SEQ ID NO: 41) | N/A |

TABLE 2b

ZFN Target sites in the human PD1 gene

| SBS# | Target site |
|---|---|
| 12942 | ccAGGGCGCCTGTGGGAtctgcatgcct (SEQ ID NO: 85) |
| 12946 | caGTCGTCTGGGCGGTGctacaactggg (SEQ ID NO: 86) |
| 12947 | caGTCGTCTGGGCGGTGctacaactggg (SEQ ID NO: 86) |
| 12934 | gaACACAGGCACGGctgaggggtcctcc (SEQ ID NO: 87) |
| 12971 | ctGTGGACTATGGGGAGCTGgatttcca (SEQ ID NO: 88) |
| 12972 | ctGTGGACTATGGGGAGCTGgatttcca (SEQ ID NO: 88) |
| 18759 | caGTCGTCTGGGCGGTGct (SEQ ID NO: 89) |
| 22237 | ccAGGGCGCCTGTGGGAtctgcatgcct (SEQ ID NO: 85) |
| 25005 | caGTCGTCTGGGCGGTGct (SEQ ID NO: 89) |
| 25006 | caGTCGTCTGGGCGGTGct (SEQ ID NO: 89) |
| 25010 | caGTCGTCTGGGCGGTGct (SEQ ID NO: 89) |
| 25011 | caGTCGTCTGGGCGGTGct (SEQ ID NO: 89) |
| 25012 | caGTCGTCTGGGCGGTGct (SEQ ID NO: 89) |
| 25013 | caGTCGTCTGGGCGGTGct (SEQ ID NO: 89) |
| 25014 | caGTCGTCTGGGCGGTGct (SEQ ID NO: 89) |
| 25015 | caGTCGTCTGGGCGGTGct (SEQ ID NO: 89) |
| 25016 | caGTCGTCTGGGCGGTGct (SEQ ID NO: 89) |
| 25017 | caGTCGTCTGGGCGGTGct (SEQ ID NO: 89) |
| 25022 | caGTCGTCTGGGCGGTGct (SEQ ID NO: 89) |
| 25023 | caGTCGTCTGGGCGGTGct (SEQ ID NO: 89) |
| 25025 | caGTCGTCTGGGCGGTGct (SEQ ID NO: 89) |
| 25027 | caGTCGTCTGGGCGGTGct (SEQ ID NO: 89) |
| 25028 | caGTCGTCTGGGCGGTGct (SEQ ID NO: 89) |
| 25029 | caGTCGTCTGGGCGGTGct (SEQ ID NO: 89) |
| 25030 | caGTCGTCTGGGCGGTGct (SEQ ID NO: 89) |
| 25031 | caGTCGTCTGGGCGGTGct (SEQ ID NO: 89) |
| 25032 | caGTCGTCTGGGCGGTGct (SEQ ID NO: 89) |
| 25034 | caGTCGTCTGGGCGGTGct (SEQ ID NO: 89) |
| 25036 | caGTCGTCTGGGCGGTGct (SEQ ID NO: 89) |
| 25040 | caGTCGTCTGGGCGGTGct (SEQ ID NO: 89) |
| 25041 | caGTCGTCTGGGCGGTGct (SEQ ID NO: 89) |

TABLE 2c

Human CTLA-4-targeted zinc finger proteins

| SBS # | F1 | F2 | F3 | F4 | F5 |
|---|---|---|---|---|---|
| 20186 | QSSDLSR (SEQ ID NO: 1) | RSDNLRE (SEQ ID NO: 2) | RSDDLSK (SEQ ID NO: 3) | QSSDLRR (SEQ ID NO: 4) | LKQHLNE (SEQ ID NO: 5) |
| 20185 | DRSALSR (SEQ ID NO: 6) | RSDALAR (SEQ ID NO: 7) | QSGDRNK (SEQ ID NO: 8) | DRSNLSR (SEQ ID NO: 9) | RSDDRKT (SEQ ID NO: 10) |
| 20190 | QSGSLTR (SEQ ID NO: 11) | RSDNLTT (SEQ ID NO: 12) | QNATRIK (SEQ ID NO: 13) | RSDVLSA (SEQ ID NO: 14) | DRSNRIK (SEQ ID NO: 15) |
| 20189 | RSANLAR (SEQ ID NO: 16) | TNQNRIT (SEQ ID NO: 17) | TSGHLSR (SEQ ID NO: 18) | RSDSLLR (SEQ ID NO: 19) | RNDDRKK (SEQ ID NO: 20) |

TABLE 3

ZFN Target sites in the human CTLA-4 genes

| SBS# | Target site | |
|---|---|---|
| 20186 | acAGTGCTTCGgCAGGCTgacagccagg | (SEQ ID NO: 21) |
| 20185 | acCCGGACcTCAGTGGCTtttgcctggag | (SEQ ID NO: 22) |
| 20190 | acTACCTGgGCATAGGCAacggaaccca | (SEQ ID NO: 23) |
| 20189 | tgGCGGTGGGTaCATGAGctccaccttg | (SEQ ID NO: 24) |

Initial in vitro activity assays were performed on nucleofected cell samples as described above. Briefly, the plasmids encoding ZFP-FokI fusions were introduced into K562 cells by transfection using the Amaxa™ Nucleofection kit as specified by the manufacturer. For transfection, two million K562 cells were mixed with varying amounts of each zinc-finger nuclease expression plasmid and 100 μL Amaxa™ Solution V. Cells were transfected in an Amaxa Nucleofector II™ using program T-16. Immediately following transfection, the cells were divided into two different flasks and grown in RPMI medium (Invitrogen) supplemented with 10% FBS in 5% $CO_2$ at either 30° C. or 37° C. for four days.

Figure 2:
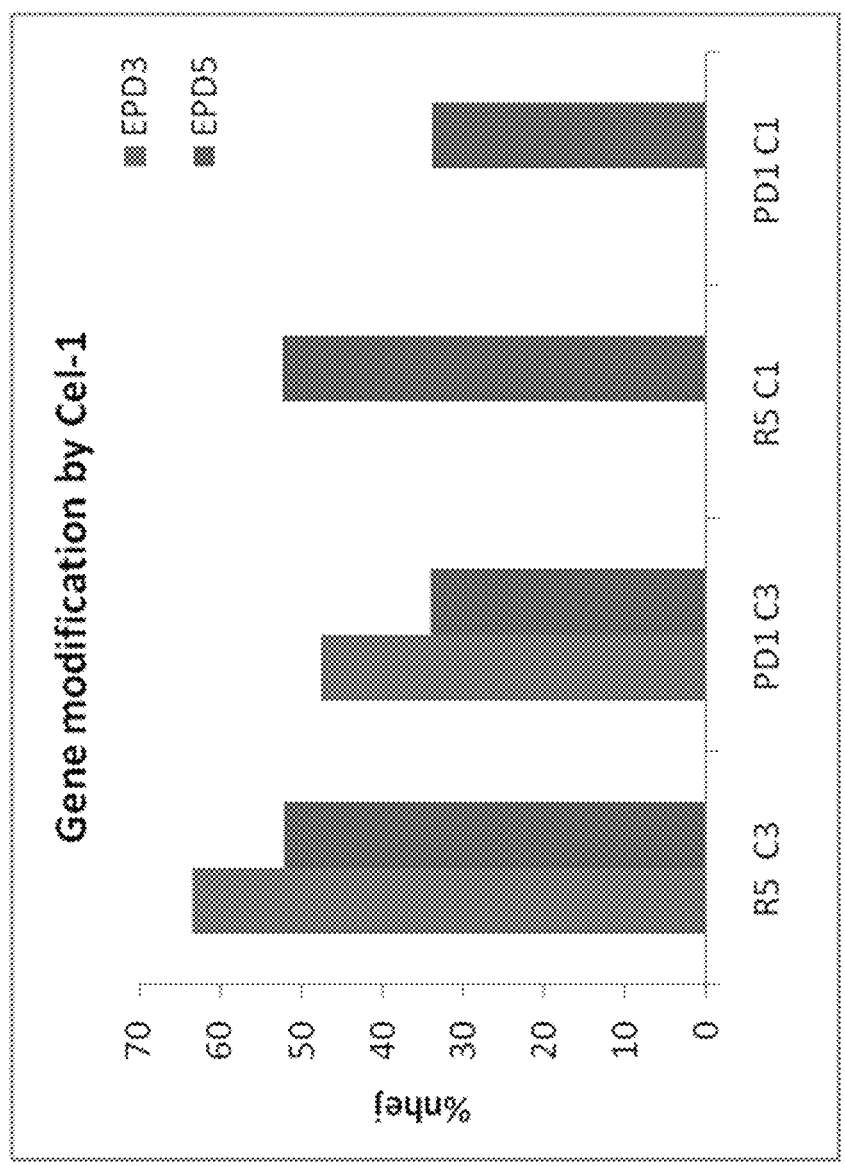
FIG. 2 is a graph depicting percent non-homologous end joining events (NHEJ) as determined by Cel-1 assay) using the indicated nucleases and conditions. "R5" refers to cells electroporated with CCR5-specific ZFN mRNA (see, e.g., U.S. Pat. No. 7,951,925). "PD1" refers to cells electroporated with PD1-specific ZFN mRNA (see, e.g., U.S. Publication No. 20110136895). "C1" and "C3" refer to electroporation conditions. The left bar of each pair shows the % NHEJ at the indicated conditions 3 days after mRNA electroporation (EPD3) and the right bar shows % NHEJ at the indicated conditions 5 days after mRNA electroporation (EPD5).

In addition, PMBCs were also activated with anti-CD28/CD38 beads (see, e.g., U.S. Publication No. 20080311095). Either 3 days (EPD3) or 5 days (EPD5) following activation, the cells were electroporated with PD1-specific ZFN mRNAs (PD1, particularly ZFNs 12942 and 25029) or CCR5 (R5, see, U.S. Pat. No. 7,951,925) using two different MAXCYTE™ conditions (C1 and C3). The cells were then analyzed for gene modification of the target locus using the CEL-1 assay described below. As shown in FIG. 2, high levels of gene modification was seen.

To determine the ZFN activity at the CTLA-4 locus, Cel-1 based SURVEYOR™ Nuclease assays were performed essentially as per the manufacturer's instructions (Transgenomic SURVEYOR™) and as described for PD1 in U.S. Patent Publication No. 20110136895. Briefly, cells were harvested and chromosomal DNA prepared using a Quickextract™ Kit according to manufacturer's directions (Epicentre®). The appropriate region of the PD1 locus was PCR amplified using Accuprime™ High-fidelity DNA polymerase (Invitrogen). PCR reactions were heated to 94° C., and gradually cooled to room temperature. Approximately 200 ng of the annealed DNA was mixed with 0.33 μL Cel-I enzyme and incubated for 20 minutes at 42° C. Reaction products were analyzed by polyacrylamide gel electrophoresis in 1× Tris-borate-EDTA buffer.

Cells were harvested 3 or 10 days after exposure to virus and gene modification efficiency was determined using a Cel-I based SURVEYOR' Nuclease assay, performed as described in International Patent Publication WO 07/014275. See, also, Oleykowski et al. (1998) *Nucleic Acids Res.* 26:4597-4602; Qui et al. (2004) *BioTechniques* 36:702-707; Yeung et al. (2005) *BioTechniques* 38:749-758.

TABLE 4

Activity of CTLA-4 ZFNs

| ZFN pair | % indels detected |
|---|---|
| 20186/20185 | 3.3% |
| 20190/20189 | 1.8% |

Example 2: PD1 and CTLA-4 Specific TALENs

PD1 specific TALENs were developed and assembled as described previously (see US Patent Publication No. 20110301073). Base recognition was achieved using the canonical RVD-base correspondences (the "TALE code": NI for A, HD for C, NN for G (NK in half repeat), NG for T). The TALENs were constructed in the "+63" TALEN backbone as described in U.S. Publication No. 20110301073. The targets and numeric identifiers for the TALENs tested are shown below in Tables 5a and 5b.

TABLE 5a

PD1 specific TALENs-Target site

| SBS # | site | # of RVDs | SEQ ID NO: |
|---|---|---|---|
| 101621 | gtAGCACCGCCCAGACGACtg | 17 | 25 |
| 101618 | gtGCTCCAGGCATGCAGATcc | 17 | 26 |
| 101620 | atGCAGATCCCACAGGCgc | 15 | 27 |
| 101622 | gtTGTAGCACCGCCCAGACga | 17 | 28 |
| 101623 | gtTGTAGCACCGCCCAGACg | 16 | 29 |
| 101624 | atGCAGATCCCACAGGCgc | 15 | 27 |
| 101625 | gtTGTAGCACCGCCCAGACga | 17 | 28 |
| 101626 | ctTCTCCCCAGCCCTGCTCgt | 17 | 30 |
| 101627 | gtGAAGGTGGCGTTGTCCCct | 17 | 31 |
| 101632 | ctACCTCTGTGGGGCCATCtc | 17 | 32 |
| 101633 | ctCTCTTTGATCTGCGCCTtg | 17 | 33 |
| 101638 | gtACCGCATGAGCCCCAGCaa | 17 | 122 |
| 101639 | ctCGGGGAAGGCGGCCAGCtt | 17 | 123 |
| 101640 | ctACCTCTGTGGGGCCATCtc | 17 | 32 |
| 101641 | ctCTCTTTGATCTGCGCCTtg | 17 | 33 |

TABLE 5b

| SBS # | # of RVDs | RVDs (N->C) |
|---|---|---|
| 101621 | 17 | NI-NN-HD-NI-HD-HD-NN-HD-HD-HD-NI-NN-NI-HD-NN-NI-HD |
| 101618 | 17 | NN-HD-NG-HD-HD-NI-NN-NN-HD-NI-NG-NN-HD-NI-NN-NI-NG |
| 101620 | 15 | NN-HD-NI-NN-NI-NG-HD-HD-HD-NI-HD-NI-NN-NN-HD |
| 101622 | 17 | NG-NN-NG-NI-NN-HD-NI-HD-HD-NN-HD-HD-HD-NI-NN-NI-HD |
| 101623 | 16 | NG-NN-NG-NI-NN-HD-NI-HD-HD-NN-HD-HD-HD-NI-NN-NI |
| 101624 | 15 | NN-HD-NI-NN-NI-NG-HD-HD-HD-NI-HD-NI-NN-NN-HD- |
| 101625 | 17 | NG-NN-NG-NI-NN-HD-NI-HD-HD-NN-HD-HD-HD-NI-NN-NI-HD |
| 101626 | 17 | NG-HD-NG-HD-HD-HD-HD-NI-NN-HD-HD-HD-NG-NN-HD-NG-HD |

TABLE 5b-continued

| SBS # | # of RVDs | RVDs (N->C) |
|---|---|---|
| 101627 | 17 | NN-NI-NI-NN-NN-NG-NN-NN-HD-NN-NG-NG-NN-NG-HD-HD-HD |
| 101632 | 17 | NI-HD-HD-NG-HD-NG-NN-NG-NN-NN-NN-NN-HD-HD-NI-NG-HD |
| 101633 | 17 | HD-NG-HD-NG-NG-NG-NN-NI-NG-HD-NG-NN-HD-NN-HD-HD-NG |
| 101638 | 17 | NI-HD-HD-NN-HD-NI-NG-NN-NI-NN-HD-HD-HD-HD-NI-NN-HD |
| 101639 | 17 | HD-NN-NN-NN-NI-NI-NN-NN-HD-NN-NN-HD-NN-NI-NN-HD |
| 101640 | 17 | NI-HD-HD-NG-HD-NG-NN-NG-NN-NN-NN-NN-HD-HD-NI-NG-HD |
| 101641 | 17 | HD-NG-HD-NG-NG-NG-NN-NI-NG-HD-NG-NN-HD-NN-HD-ND-NG |

The TALENs were then tested in pairs in K562 cells for the ability to induce modifications at the endogenous PD1 chromosomal targets, and the results showed that nearly all protein pairs were active. Side by side activity comparisons with the 12942/25029 ZFN pair (see U.S. Patent Publication No. 2011-136895) shown below in Table 6, showed that the TALENs and ZFNs have activities that are in the same approximate range. Note that the Lane numbers shown in Table 6 correspond to the lanes shown in FIG. 1.

TABLE 6

| PD1 TALEN activity | | |
|---|---|---|
| Lane | TALEN pair | % NHEJ |
| 1 | 101621/101618 | 23.5 |
| 2 | 101621/101619 | 18.1 |
| 3 | 101621/101620 | 0 |
| 4 | 101622/101618 | 14.7 |
| 5 | 101622/101619 | 14.7 |
| 6 | 101622/101620 | 10.6 |
| 7 | 101623/101618 | 6.8 |
| 8 | 101623/101619 | 18.2 |
| 9 | 101623/101620 | 11.6 |
| 10 | 101625/101624 | 10.1 |

TABLE 6-continued

| PD1 TALEN activity | | |
|---|---|---|
| Lane | TALEN pair | % NHEJ |
| 11 | 12942/25029 (ZFN) | 14.7 |
| G | GFP | 0 |
| 12 | 101627/101626 | 12.5 |
| 13 | 101633/101632 | 14.7 |
| 14 | 101639/101638 | 0 |
| 15 | 101641/101640 | 23 |
| G | GFP | 0 |

CTLA-4 specific TALENs are designed and assembled as described above. Testing for activity on the endogenous CTLA-4 chromosomal target reveals that the TALENs are active.

Example 3: Generation of T-Cells Comprising a CAR that Also Lack PD1 and/or CTLA-4

To generate a T-cell population that expresses a CAR and in which PD1 and/or CTLA-4 are knocked out, CAR containing T-cells are generated. Cells (e.g., PBMCs, T-cells such as TILs, CD4+ or CD8+ cells) are purified from natural sources, for example, a metastatic melanoma patient, and cultured and/or expanded according to standard procedures. Cells may be stimulated, for example, as described in U.S. Patent Publication No. 20080311095. Cells are transduced with CAR, for example a CAR comprising either an ErbB2-specific scFv or a VEGFR2-specific scFv. The nucleic acids encoding the scFvs are first constructed via a PCR approach and are sequence verified. They are linked to CD28 and CD3 zeta signaling moieties and introduced into the cells (e.g., via retroviral or lentiviral or other targeting/delivery mechanisms).

The cells are then treated with mRNAs encoding PD1 and/or CTLA-4-specific nucleases and the population is analyzed by the Cel-I assay to verify PD1 or CTLA-4 disruption and CAR insertion. The engineered T-cells are then tested on tumor cell lines expressing either ErbB2 or VEGF2R and shown to specifically lyse these target cell lines.

Example 4: PD1 Specific ZFP TFs

PD1 specific ZFP TFs were designed to repress expression of PD1 expression. These proteins are shown below in Table 7a and 7b.

TABLE 7a

| Human PD1-targeted zinc finger proteins for ZFP-TFs | | | | | | |
|---|---|---|---|---|---|---|
| | Design | | | | | |
| SBS # | F1 | F2 | F3 | F4 | F5 | F6 |
| 22937 | RSDTLSV (SEQ ID NO: 101) | DNSTRIK (SEQ ID NO: 102) | RSDHLSQ (SEQ ID NO: 49) | RSDVRKN (SEQ ID NO: 103) | DRSHLTR (SEQ ID NO: 104) | RSDNLTT (SEQ ID NO: 12) |
| 22945 | RSDDLTR (SEQ ID NO: 37) | RSDHLSR (SEQ ID NO: 105) | RSDNLAR (SEQ ID NO: 106) | QSGNLAR (SEQ ID NO: 107) | RSDNLAR (SEQ ID NO: 106) | RSDALAR (SEQ ID NO: 7) |
| 22954 | QSGDLTR (SEQ ID NO: 108) | RSDDLTR (SEQ ID NO: 37) | RSDNLSV (SEQ ID NO: 109) | RSANLTR (SEQ ID NO: 48) | RSDVLSK (SEQ ID NO: 110) | QNATRIK (SEQ ID NO: 13) |
| 22957 | RSDVLSE (SEQ ID NO: 47) | ARSTRTN (SEQ ID NO: 111) | DRSHLTR (SEQ ID NO: 104) | DRSHLAR (SEQ ID NO: 112) | QSGNLAR (SEQ ID NO: 107) | QSGHLSR (SEQ ID NO: 34) |

TABLE 7a-continued

Human PD1-targeted zinc finger proteins for ZFP-TFs

| | | | Design | | | |
|---|---|---|---|---|---|---|
| SBS # | F1 | F2 | F3 | F4 | F5 | F6 |
| 22959 | RSDNLSE (SEQ ID NO: 113) | DRSHLAR (SEQ ID NO: 112) | DRSHLTR (SEQ ID NO: 104) | QSSDLRR (SEQ ID NO: 4) | RSDHLST (SEQ ID NO: 114) | DRSNRKT (SEQ ID NO: 115) |

TABLE 7b

Human PD1-targeted zinc finger proteins for ZFP-TFs, target sites

| SBS# | Target site |
|---|---|
| 22937 | ggTAGGGCGTGGGGGCCACGggcccacc_ (SEQ ID NO: 116) |
| 22945 | atGTGGAGGAAGAGGGGGCGggagcaag_ (SEQ ID NO: 117) |
| 22954 | gaGCAGTGGAGAAGGCGGCActctggtg_ (SEQ ID NO: 118) |
| 22957 | gtGGAGAAGGCGGCACTCTGgtggggct_ (SEQ ID NO: 119) |
| 22959 | acAACTGGGCTGGCGGCCAGgatggttc_ (SEQ ID NO: 120) |

The PD1-specific DNA binding domains depicted in Table 7a were then fused to a KRAB repression domain from the human KOX1 gene. To test the activity of the PD1 repressing ZFP TFs, the ZFP TFs were transfected into human cells and expression of PD1 was monitored using real-time RT-PCR. Specifically, Jurkat cells were cultured in DMEM supplemented with 10% FBS and $1e^5$ cells are transfected with 1 μg of plasmid DNA encoding indicated ZFP-KOX fusions by Amaxa Nucleofector® following the manufacturer's instructions.

Transfected cells were incubated for 2 days, and the levels of endogenous human PD1 and normalization control 18S were analyzed by real-time PCR (Applied Biosystems), according to standard protocols. PD1 levels were expressed as PD1/18S ratios normalized to that of the mock-transfected samples (set as 1).

PD1-Targeted ZFPs Repressed PD1 Expression.

Western blot analyses are done using standard protocols to confirm the reduction in PD1 protein level.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. An isolated genetically modified human T-cell that comprises:
   (I) an exogenous sequence encoding a chimeric antigen receptor (CAR) integrated into an endogenous programmed death receptor PDCD1 (PD1) or CTLA-4 gene; and
   (II)
   (a) a pair of zinc finger nucleases (ZFNs) that cleave the PD1 gene, the pair comprising:
   (i) ZFN 12942 comprising five zinc finger domains designated F1 to F5, each domain comprising a recognition helix region ordered as follows:
   F1: QSGHLSR (SEQ ID NO:34);
   F2: RSDSLSV (SEQ ID NO:35);
   F3: HNDSRKN (SEQ ID NO:36);
   F4: RSDDLTR (SEQ ID NO:37); and
   F5: RSDHLTQ (SEQ ID NO:38); and
   ZFN 12946 comprising five zinc finger domains designated F1 to F5, each domain comprising a recognition helix region ordered as follows:
   F1: RSAALSR (SEQ ID NO:39);
   F2: RSDDLTR (SEQ ID NO:37);
   F3: RSDHLTT (SEQ ID NO:40);
   F4: DRSALSR (SEQ ID NO:6); and
   F5: DRSALAR (SEQ ID NO:41); or
   (ii) ZFN 12942 and
   ZFN 12947 comprising five zinc finger domains designated F1 to F5, each domain comprising a recognition helix region ordered as follows:
   F1: RSAALAR (SEQ ID NO:42);
   F2: RSDDLSK (SEQ ID NO:3);
   F3: RNDHRKN (SEQ ID NO:43);
   F4: DRSALSR (SEQ ID NO:6); and
   F5: DRSALAR (SEQ ID NO:41); or
   (iii) ZFN 12934 comprising four zinc finger domains designated F1 to F4, each domain comprising a recognition helix region ordered as follows:
   F1: RSDHLSE (SEQ ID NO:44);
   F2: TSSDRTK (SEQ ID NO:45);
   F3: RSDHLSE (SEQ ID NO:44); and
   F4: QSASRKN (SEQ ID NO:46); and
   ZFN 12971 comprising six finger domains designated F1 to F6, each domain comprising a recognition helix region ordered as follows:
   F1: RSDVLSE(SEQ ID NO:47);
   F2: RSANLTR (SEQ ID NO:48);
   F3: RSDHLSQ (SEQ ID NO:49);
   F4: TSSNRKT (SEQ ID NO:50);
   F5: DRSNLSR (SEQ ID NO:9); and
   F6: RSDALAR (SEQ ID NO:7); or
   (iv) ZFN 12934 and
   ZFN 12972 comprising six finger domains designated F1 to F6, each domain comprising a recognition helix region as follows:
   F1: DDWNLSQ (SEQ ID NO:51);
   F2: RSANLTR (SEQ ID NO:48);
   F3: RSDHLSQ (SEQ ID NO:49);
   F4: TSSNRKT (SEQ ID NO:50);
   F5: DRSNLSR (SEQ ID NO:9); and
   F6: RSDALAR(SEQ ID NO:7); or
   (v) ZFN 12942 and
   ZFN 25029 comprising five zinc finger domains designated F1 to F5, each domain comprising a recognition helix region ordered as follows:
   F1: RNAALTR (SEQ ID NO:73);
   F2: RSDELTR (SEQ ID NO:57);
   F3: RHHHLAA (SEQ ID NO:77);
   F4: TRPVLKR (SEQ ID NO:54); and
   F5: DRSALAR (SEQ ID NO:41); or
   (b) a pair of transcription activator-like effector nucleases (TALENs) that cleave the PD1 gene, wherein the pair of TALENs comprises:
   (i) a TALEN comprising 17 TALE repeat units comprising the following repeat variable diresidues (RVDs): NI-NN-HD-NI-HD-HD-NN-HD-HD-HD-NI-NN-NI-HD-NN-NI-HD and
   a TALEN comprising 17 TALE repeat units comprising the following RVDs: NN-HD-NG-HD-HD-NI-NN-NN-HD-NI-NG-NN-HD-NI-NN-NI-NG; or
   (ii) a TALEN comprising 17 TALE repeat units comprising the following RVDs: NG-NN-NG-NI-NN-HD-NI-HD-HD-NN-HD-HD-HD-NI-NN-NI-HD; and
   a TALEN comprising 17 TALE repeat units comprising the following RVDs: NN-HD-NG-HD-HD-NI-NN-NN-HD-NI-NG-NN-HD-NI-NN-NI-NG or a TALEN comprising 15 TALE repeat units comprising the following RVDs: NN-HD-NI-NN-NI-NG-HD-HD-HD-NI-HD-NI-NN-NN-HD; or
   (iii) a TALEN comprising 16 TALE repeat units comprising the following RVDs: NG-NN-NG-NI-NN-HD-NI-HD-HD-NN-HD-HD-HD-NI-NN-NI; and
   a TALEN comprising 17 TALE repeat units comprising the following RVDs: NN-HD-NG-HD-HD-NI-NN-NN-HD-NI-NG-NN-HD-NI-NN-NI-NG or a TALEN comprising 15 TALE repeat units comprising the following RVDs: NN-HD-NI-NN-NI-NG-HD-HD-HD-NI-HD-NI-NN-NN-HD; or
   (iv) a TALEN comprising 17 TALE repeat units comprising the following RVDs: NN-NINI-NN-NN-NG-NN-NN-HD-NN-NG-NG-NN-NG-HD-HD-HD; and
   a TALEN comprising 17 TALE repeat units comprising the following RVDs: NG-HD-NG-HD-HD-HD-HD-NI-NN-HD-HD-HD-NG-NN-HD-NG-HD; or
   (v) a TALEN comprising 17 TALE repeat units comprising the following RVDs: HD-NG-HD-NG-NG-NG-NN-NI-NG-HD-NG-NN-HD-NN-HD-HD-NG; and
   a TALEN comprising 17 TALE repeat units comprising the following RVDs: NI-HD-HD-NG-HD-NG-NN-NG-NN-NN-NN-NN-HD-HD-NI-NG-HD; or
   (c) a pair of ZFNs that cleave the CTLA-4 gene, the pair comprising:
   (i) ZFN 20186 comprising five zinc finger domains designated F1 to F5, each domain comprising a recognition helix region ordered as follows:
   F1: QSSDLSR (SEQ ID NO:1);
   F2: RSDNLRE (SEQ ID NO:2);
   F3: RSDDLSK (SEQ ID NO:3);
   F4: QSSDLRR (SEQ ID NO:4); and
   F5: LKQHLNE (SEQ ID NO:5); and
   ZFN 20185 comprising five zinc finger domains designated F1 to F5, each domain comprising a recognition helix region ordered as follows:
   F1: DRSALSR (SEQ ID NO:6);
   F2: RSDALAR (SEQ ID NO:7);
   F3: QSGDRNK (SEQ ID NO:8);
   F4: DRSNLSR (SEQ ID NO:9); and
   F5: RSDDRKT (SEQ ID NO:10); or
   (ii) ZFN 20190 comprising five zinc finger domains designated F1 to F5, each domain comprising a recognition helix region ordered as follows:
   F1: QSGSLTR (SEQ ID NO:11);
   F2: RSDNLTT (SEQ ID NO:12);
   F3: QNATRIK (SEQ ID NO:13);

F4: RSDVLSA (SEQ ID NO:14); and
F5: DRSNRIK (SEQ ID NO:15); and
ZFN 20189 comprising five zinc finger domains designated F1 to F5, each domain comprising a recognition helix region ordered as follows:
F1: RSANLAR (SEQ ID NO:16);
F2: TNQNRIT (SEQ ID NO:17);
F3: TSGHLSR (SEQ ID NO:18);
F4: RSDSLLR (SEQ ID NO:19); and
F5: RNDDRKK (SEQ ID NO:20).

2. The T-cell of claim 1 wherein the CAR is integrated into the CTLA-4 gene.

3. The T-cell of claim 1, wherein the CAR is integrated into the PD1 gene.

4. The T-cell of claim 1, wherein the T-cell is selected from the group consisting of a CD4+ cell, a CD8+ cell and a tumor infiltrating cell (TIL).

5. The T-cell of claim 1, wherein the CAR comprises a signaling domain of a T-cell receptor (TCR).

6. The T-cell of claim 5, wherein the CAR comprises a scFv specificity domain.

7. The T-cell of claim 1, further comprising at least one additional transgene.

8. The T-cell of claim 7, wherein the at least one additional transgene encodes a tumor-associated antigen (TAA)-specific T-cell receptor (TCR).

9. The T-cell of claim 1, wherein the T-cell is stimulated.

10. The T-cell of claim 9, wherein the T-cell is stimulated with anti-CD28/CD3 beads.

11. A pair of zinc finger nucleases that cleave the CTLA-4 gene, wherein the pair of zinc finger nucleases are:
(i) ZFN 20186 comprising five zinc finger domains designated F1 to F5, each domain comprising a recognition helix region ordered as follows:
F1: QSSDLSR (SEQ ID NO:1);
F2: RSDNLRE (SEQ ID NO:2);
F3: RSDDLSK (SEQ ID NO:3);
F4: QSSDLRR (SEQ ID NO:4); and
F5: LKQHLNE (SEQ ID NO:5); and
ZFN 20185 comprising five zinc finger domains designated F1 to F5, each domain comprising a recognition helix region ordered as follows:
F1: DRSALSR (SEQ ID NO:6);
F2: RSDALAR (SEQ ID NO:7);
F3: QSGDRNK (SEQ ID NO:8);
F4: DRSNLSR (SEQ ID NO:9); and
F5: RSDDRKT (SEQ ID NO:10); or
(ii) ZFN 20190 comprising five zinc finger domains designated F1 to F5, each domain comprising a recognition helix region ordered as follows:
F1: QSGSLTR (SEQ ID NO:11);
F2: RSDNLTT (SEQ ID NO:12);
F3: QNATRIK (SEQ ID NO:13);
F4: RSDVLSA (SEQ ID NO:14); and
F5: DRSNRIK (SEQ ID NO:15); and
ZFN 20189 comprising five zinc finger domains designated F1 to F5, each domain comprising a recognition helix region ordered as follows:
F1: RSANLAR (SEQ ID NO:16);
F2: TNQNRIT (SEQ ID NO:17);
F3: TSGHLSR (SEQ ID NO:18);
F4: RSDSLLR (SEQ ID NO:19); and
F5: RNDDRKK (SEQ ID NO:20).

12. A pair of TALENs that cleave the PD1 gene, wherein the pair of TALENs are:
(i) a TALEN comprising 17 TALE repeat units comprising the following repeat variable diresidues (RVDs): NI-NN-HD-NI-HD-HD-NN-HD-HD-HD-NI-NN-NI-HD-NN-NI-HD; and
a TALEN comprising 17 TALE repeat units comprising the following RVDs: NN-HD-NG-HD-HD-NI-NN-NN-HD-NI-NG-NN-HD-NI-NN-NI-NG; or
(ii) a TALEN comprising 17 TALE repeat units comprising the following RVDs: NG-NN-NG-NI-NN-HD-NI-HD-HD-NN-HD-HD-HD-NI-NN-NI-HD; and
a TALEN comprising 17 TALE repeat units comprising the following RVDs: NN-HD-NG-HD-HD-NI-NN-NN-HD-NI-NG-NN-HD-NI-NN-NI-NG OR a TALEN comprising 15 TALE repeat units comprising the following RVDs: NN-HD-NI-NN-NI-NG-HD-HD-HD-NI-HD-NI-NN-NN-HD; or
(iii) a TALEN comprising 16 TALE repeat units comprising the following RVDs: NG-NN-NG-NI-NN-HD-NI-HD-HD-NN-HD-HD-HD-NI-NN-NI; and
a TALEN comprising 17 TALE repeat units comprising the following RVDs: NN-HD-NG-HD-HD-NI-NN-NN-HD-NI-NG-NN-HD-NI-NN-NI-NG or a TALEN comprising 15 TALE repeat units comprising the following RVDs: NN-HD-NI-NN-NI-NG-HD-HD-HD-NI-HD-NI-NN-NN-HD; or
(iv) a TALEN comprising 17 TALE repeat units comprising the following RVDs: NN-NI-NI-NN-NN-NG-NN-NN-HD-NN-NG-NG-NN-NG-HD-HD-HD; and
a TALEN comprising 17 TALE repeat units comprising the following RVDs: NG-HD-NG-HD-HD-HD-HD-NI-NN-HD-HD-HD-NG-NN-HD-NG-HD; or
(v) a TALEN comprising 17 TALE repeat units comprising the following RVDs: HD-NG-HD-NG-NG-NG-NN-NI-NG-HD-NG-NN-HD-NN-HD-HD-NG; and
a TALEN comprising 17 TALE repeat units comprising the following RVDs: NI-HD-HD-NG-HD-NG-NN-NG-NN-NN-NN-NN-HD-HD-NI-NG-HD.

* * * * *